United States Patent
Párta et al.

(10) Patent No.: US 12,168,791 B2
(45) Date of Patent: Dec. 17, 2024

(54) METHOD FOR MODIFYING THE GLYCOSYLATION PROFILE OF A RECOMBINANT GLYCOPROTEIN PRODUCED IN CELL CULTURE

(71) Applicant: RICHTER GEDEON NYRT., Budapest (HU)

(72) Inventors: László Párta, Saint-Louis (FR); Ákos Putics, Budapest (HU); Tibor Balogh, Budapest (HU); Balázs Horváth, Ajka (HU); Gáspár Nagy, Gyömr (HU)

(73) Assignee: RICHTER GEDEON NYRT., Budapest (HU)

( * ) Notice: Subject to any disclaimer, the term of this patent is extended or adjusted under 35 U.S.C. 154(b) by 762 days.

(21) Appl. No.: 17/292,302

(22) PCT Filed: Nov. 6, 2019

(86) PCT No.: PCT/EP2019/080342
§ 371 (c)(1),
(2) Date: May 7, 2021

(87) PCT Pub. No.: WO2020/094694
PCT Pub. Date: May 14, 2020

(65) Prior Publication Data
US 2022/0098634 A1     Mar. 31, 2022

(30) Foreign Application Priority Data
Nov. 7, 2018 (HU) ..................................... 1800376

(51) Int. Cl.
*C12P 21/00* (2006.01)
*C12N 5/00* (2006.01)

(52) U.S. Cl.
CPC .......... *C12P 21/005* (2013.01); *C12N 5/0043* (2013.01); *C12N 2500/20* (2013.01); *C12N 2500/33* (2013.01); *C12N 2500/34* (2013.01); *C12N 2511/00* (2013.01)

(58) Field of Classification Search
CPC . C12P 21/005; C12N 5/0043; C12N 2500/20; C12N 2500/33; C12N 2500/34; C12N 2511/00; C12N 2500/32; C12N 5/0018; C12N 5/00; C12N 15/85; C12N 2500/10; C07K 2317/14; C07K 16/22; C07K 16/2887; C07K 2317/41; C07K 16/00; A61K 2039/505
See application file for complete search history.

(56) References Cited

U.S. PATENT DOCUMENTS

| | | |
|---|---|---|
| 4,560,855 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,489 A | 6/1992 | Mather et al. |
| 8,129,145 B2 | 3/2012 | Lasko et al. |
| 10,017,732 B2 | 7/2018 | Vijayasankaran et al. |
| 2017/0166941 A1 | 6/2017 | Jung et al. |
| 2018/0223249 A1* | 8/2018 | Johnson ............... C12N 5/0018 |
| 2018/0230228 A1 | 8/2018 | Putics et al. |
| 2018/0251572 A1* | 9/2018 | Misaghi ................. C07K 16/44 |

FOREIGN PATENT DOCUMENTS

| | | |
|---|---|---|
| CN | 104878064 A | 9/2015 |
| CN | 106029871 A | 10/2016 |
| EP | 2495301 A1 | 9/2012 |
| EP | 2495307 A1 | 9/2012 |
| JP | 2009543550 A | 12/2009 |
| JP | 2016514461 A | 5/2016 |
| JP | 2017538446 A | 12/2017 |
| JP | 2018521664 A | 8/2018 |
| JP | 2018521676 A | 8/2018 |
| WO | WO87/00195 A1 | 1/1987 |
| WO | WO90/03430 A1 | 4/1990 |
| WO | WO92/16553 A1 | 10/1992 |
| WO | WO92/22653 A1 | 12/1992 |
| WO | WO94/11026 A2 | 5/1994 |
| WO | WO97/29131 A1 | 8/1997 |
| WO | WO98/45331 A2 | 10/1998 |
| WO | WO03/002713 A2 | 1/2003 |
| WO | WO2010/138502 A3 | 2/2011 |
| WO | WO2012/149197 A2 | 11/2012 |

(Continued)

OTHER PUBLICATIONS

Hossler et al. 2009, "Optimal and consistent protein glycosylation in mammalian cell culture." Glycobiology vol. 19, 9, pp. 936-949, doi: doi.org/10.1093/glycob/cwp079 (Year: 2009).*

Radhakrishnan et al. 2017, "Controlling the Glycosylation Profile in mAbs Using Time-Dependent Media Supplementation." Antibodies(Basel, Switzerland)7(1), 1., pp. 1-21, doi: doi.org/10.3390/antib7010001 (Year: 2017).*

Baenziger, J.U., "5—The Oligosaccharides of Plasma Glycoproteins: Synthesis, Structure, and Function", The Plasma Proteins (Second Edition), Ed. by Putnam, F.W., Structure, Function, and Genetic Control, Academic Press. 1984. pp. 271-315.

Barnes, D., et al., "Methods for growth of cultured cells in serum-free medium", Anal. Biochem., vol. 102, 1980, pp. 255-270.

Deutscher, M.P., et al., "Guide to Protein Purification: Methods in Enzymology", Methods in Enzymology Series, vol. 182, Academic Press, 1997, pp. 461.

(Continued)

*Primary Examiner* — Terry A McKelvey
*Assistant Examiner* — Andrew T Moehlman
(74) *Attorney, Agent, or Firm* — Sterne, Kessler, Goldstein & Fox P.L.L.C.

(57) ABSTRACT

The present invention relates to a method for modifying the glycosylation profile of a recombinant glycoprotein produced in cell culture comprising culturing eukaryotic cells expressing the recombinant glycoprotein in a cell culture medium, wherein the cell culture medium is supplemented with fucose, manganese, and taurine, wherein the glycosylation profile of the produced recombinant glycoprotein is modified to better resemble the glycosylation profile of a reference glycoprotein than when cultured without said supplementation.

21 Claims, 3 Drawing Sheets

(56) References Cited

FOREIGN PATENT DOCUMENTS

| WO | WO2013/114245 A1 | 8/2013 | |
| WO | WO2015/011660 A1 | 1/2015 | |
| WO | WO2015/128314 A1 | 9/2015 | |
| WO | WO2016/089919 A1 | 6/2016 | |
| WO | WO-2016196621 A1 * | 12/2016 | ......... C07K 16/2842 |
| WO | WO2017/021871 A1 | 2/2017 | |
| WO | WO2017/024062 A1 | 2/2017 | |
| WO | WO2017/079165 A1 | 5/2017 | |
| WO | WO2017/120359 A1 | 7/2017 | |
| WO | WO-2017120347 A1 * | 7/2017 | .......... C07K 16/241 |
| WO | WO2017/134667 A1 | 8/2017 | |
| WO | WO2020/094694 A1 | 5/2020 | |

OTHER PUBLICATIONS

Grabenhorst, E., et al., "Genetic engineering of recombinant glycoproteins and the glycosylation pathway in mammalian host cells", Glycoconjug. J., vol. 16, 1999, pp. 81-97.

Graham, F.L., et al., "Characteristics of a human cell line transformed by DNA from human adenovirus type 5", J. Gen Virol., vol. 36. 1977, pp. 59-74.

Gramer, M.J., et al., "Modulation of antibody galactosylation through feeding of undine, manganese chloride, and galactose", Biotechnol Bioeng, vol. 108, 2011, pp. 1591-1602.

Ham, R.G., et al., "Media and growth requirements", Methods Enzymol., vol. 58, 1979, pp. 44-93.

Higgins, S. J., et al., "Protein Expression: A Practical Approach", Oxford Univ Press, 1999, p. 296.

Ho, D.E., et al., "Fucosylation of a Therapeutic Antibody: Effects on Antibody-Dependent, Cell-Mediated Cytotoxicity (ADCC) Potency and Efficacy", BioProcess International; vol. 14, No. 4, 2016, pp. 8.

Huang, Y.-M., et al., "Maximizing productivity of CHO cell-based fed-batch culture using chemically defined media conditions and typical manufacturing equipment", Biotechnology Progress, vol. 26, No. 5, 2010, pp. 1400-1410.

James, D.C., et al., "Encyclopedia of bioprocess technology: Fermentation, biocatalysis and bioseparation", New York: John Wiley & Sons. 1999, pp. 1336-1349.

James, D.C., et al., "N-Glycosylation of Recombinant Human Interferon-γ Produced in Different Animal Expression Systems", Nature biotechnology, vol. 13, 1995, pp. 592-596.

Jefferis, R., et al., "IgG-Fc-mediated effector functions: molecular definition of interaction sites for effector ligands and the role of glycosylation", Immunol Rev, vol. 163, 1998, pp. 59-76.

Jenkins, N., et al. "Getting the glycosylation right: implications for the biotechnology industry", Nature Biotechnol., vol. 14, 1996, pp. 975-981.

Konno, Y., et al., "Fucose content of monoclonal antibodies can be controlled by culture medium osmolality for high antibody-dependent cellular cytotoxicity", Cytotechnology, vol. 64, No. 3, 2012, pp. 249-265.

Lifely, M.R., et al., "Glycosylation and biological activity of CAMPATH-1H expressed in different cell lines and grown under different culture conditions", Glycobiology, vol. 5, 1995, pp. 813-822.

Luo. Y., et al., "Combined approach of NMR and chemometrics for screening peptones used in the cell culture medium for the production of a recombinant therapeutic protein", Biotechnology and Bioengineering, vol. 97, No. 6, 2007, pp. 1654-1659.

Ma, N., et al., "A single nutrient feed supports both chemically defined NSD and CHO fed-batch processes: Improved productivity and lactate metabolism", Biotechnology Progress, vol. 25 No. 5, 2009, pp. 1353-1363.

Mather, J.P., et al., "Culture of testicular cells in hormone-supplemented serum-free medium", Annals N.Y. Acad. Sci., vol. 383, 1982, pp. 44-68.

Mather, J.P., et al., "Establishment and characterization of two distinct mouse testicular epithelial cell lines", Biol. Reprod, vol. 23, 1980, pp. 243-252.

Raju, T.C., et al., "Species-specific variation in glycosylation of IgG: evidence for the species-specific sialylation and branch-specific galactosylation and importance for engineering recombinant glycoprotein therapeutics", Glycobiology, vol. 10, No. 5, 2000, pp. 477-486.

Raju, T.S., et al., "Galactosylation variations in marketed therapeutic antibodies", MAbs., vol. 4, No. 3, 2012, pp. 385-391.

Ravetch, J.V., et al., "IgG Fc receptors", Annu Rev Immunol, vol. 19, 2001, pp. 275-290.

Reusch, D., et al., "Comparison of methods for the analysis of therapeutic immunoglobulin G Fc-glycosylation profiles—part 1: separation-based methods", vol. 7, 2015, pp. 167-179.

Rudd, P.M., et al., "Glycosylation and the immune system", Science, vol. 291, 2001, pp. 2370-2376.

Scopes, R.K., et al., "Protein Purification Principles and Practice", 2nd Edition, Springer-Verlag, New York, 1987, pp. 342.

Urlaub, G., et al., "Isolation of Chinese hamster cell mutants deficient in dihydrofolate reductase activity", Natl. Acad. Sci. USA, vol. 77, 1980, pp. 4216-4220.

Yu, M., et al., "Understanding the Intracellular Effect of Enhanced Nutrient Feeding Toward High Titer Antibody Production Process", Biotechnology and Bioengineering, vol. 108, No. 5, 2010, pp. 1078-1088.

Office Action Received in Hungarian Patent Application No. 1800376 mailed on Nov. 7, 2018, 8 pages. (Translation).

International Preliminary Report on Patentability received in PCT Application No. PCT/EP2019/080342 mailed on May 20, 2021, 7 pages.

International Search Report and Written Opinion received in PCT Application No. PCT/EP2019/080342 mailed on Feb. 21, 2020, 8 pages.

Office Action received in Japanese Patent Application No. 2021524198, mailed on Jun. 6, 2023, 11 pages. (Translation).

Office Action received in Chinese Patent Application No. 201980088055.3 mailed on Jun. 29, 2023, 10 pages (Translation).

Office Action received in Canadian Patent Application No. 3118604 mailed on Aug. 18, 2023, 5 pages.

Decision of Refusal received in Japanese Patent Application No. 2021524198, mailed on Jan. 9, 2024, 12 pages (Translation).

* cited by examiner

METHOD FOR MODIFYING THE GLYCOSYLATION PROFILE OF A RECOMBINANT GLYCOPROTEIN PRODUCED IN CELL CULTURE

FIELD OF THE INVENTION

The present invention relates to a method for modifying the glycosylation profile of a recombinant glycoprotein produced in cell culture comprising culturing eukaryotic cells expressing the recombinant glycoprotein in a cell culture medium, wherein the cell culture medium is supplemented with fucose, manganese, and taurine, wherein the glycosylation profile of the produced recombinant glycoprotein is modified to better resemble the glycosylation profile of a reference glycoprotein than when cultured without said supplementation.

BACKGROUND OF THE INVENTION

Glycoproteins are essential for proper function of all arms of the immune system, including the innate and adaptive immune system. For example, glycoproteins are involved in recognition, binding, signalling, and elimination of threats via complement-dependent cytotoxicity (CDC) and antibody-dependent cell-mediated cytotoxicity (ADCC) (Rudd et al, Science, 291, 2001, 2370-2376; and Jefferis et al, Immunol Rev, 163, 1998, 59-76).

Mammalian expressed antibodies bear a single glycan on Asn residues of their heavy chain (HC). The presence and composition of the glycan structure influences the receptor binding and effector function of the antibody (Rudd et al., Science, 291, 2001, 2370-2376; and Jefferis et al., Immunol Rev, 163, 1998, 59-76). For example, variations in glycan composition of the Fc region of an IgG (Fcγ) differentially affect the binding affinity of the Fc region and Fc binding receptors (FcR). There are three classes of FcγR, namely, FcγRI, FcγRII, and FcγRIII (Jefferis et al., Immunol Rev, 163, 1998, 59-76; Ravetch & Bolland, Annu Rev Immunol, 19, 2001, 275-290). Differential affinities of an antibody and Fcγ receptors dictate the fate of the immune response of the host to a particular antigen and further may be responsible for activation, inhibition, antibody efficacy/half-life, tolerance, and the autoimmune response (Ravetch & Bolland, Annu Rev Immunol, 19, 2001, 275-290). The affinity of an antibody for different types of receptors can change depending on the presence and composition of the glycans it bears, thus highlighting the importance of oligosaccharide/protein interactions on the biological function of antibodies (Raju et al, Glycobiology, 10, 2000, 477-486; Jefferis et al, Immunol Rev, 163, 1998, 59-76).

Following the expression of proteins in eukaryotic, e.g. mammalian, host cells, the proteins undergo post-translational modifications, often including the enzymatic addition of sugar residues, generally referred to as "glycosylation". Glycosylation of polypeptides is typically either N-linked or O-linked. The attachment of the carbohydrate moiety to the side-chain of an asparagine residue is referred to as N-linked glycosylation. The tripeptide sequences asparagine (Asn)-X-serine (Ser) and asparagine (Asn)-X-threonine (Thr), wherein X is any amino acid except proline, are recognition sequences for enzymatic attachment of the carbohydrate moiety to the asparagine side chain. The attachment of one of the sugars N-acetylgalactosamine, galactose, fucose, N-acetylglucosamine, or xylose to a hydroxyamino acid, most commonly serine or threonine, although 5-hydroxyproline or 5-hydroxylysine may also be involved, is referred to as O-linked glycosylation. Glycosylation patterns for proteins produced by mammals can be subdivided into several groups, including complex, high mannose, and hybrid structures, as well as glycosidically linked oligosaccharides (The Plasma Proteins: Structure, Function and Genetic Control, Putnam, F. W., ed., 2nd edition, Vol. 4, Academic Press, New York, 1984, especially pp. 271-315.)

Over the last few decades, a large amount of research has focused on the production of therapeutic recombinant glycoproteins, such as monoclonal antibodies. While one approach in the literature has been the use of media containing sera or hydrolysates, chemically defined media were also developed in order to eliminate the problematic lot-to-lot variation of complex components (Luo and Chen, Biotechnology and Bioengineering, 97(6): 1654-1659 (2007)). An improved understanding of the cell culture has permitted a shift to chemically defined medium without compromising on growth, viability, titer, etc. Optimized, chemically defined processes with titers as high as 7.5-10 g/L have been reported (Huang et al, Biotechnology Progress 26(5): 1400-1410 (2010); Ma et al, Biotechnology Progress 25(5): 1353-1363 (2009); Yu et al, Biotechnology and Bioengineering, 108(5):1078-1088 (2011)). In general, the high titer chemically defined processes are fed-batch processes with cultivation times of 11-18 days.

A number of reports have demonstrated that processing of N-glycans associated with recombinant proteins is specific for each mammalian cell (James et al., Bio/Technology, 13:592-596 (1995); Lifely et al., Glycobiology, 5:813-822 (1995)). These differences are not only important for the production of therapeutic glycoproteins due to directly influencing the antigenicity, rate of clearance in vivo, and stability of recombinant glycoproteins (Jenkins et al., Nature Biotechnol. 14:975-981 (1996)), but also due to tight regulatory standards that must be met for any given approved therapeutic glycoprotein. Thus, it is important not only to be able to characterize glycans bound to a therapeutic recombinant glycoprotein to predict the consequences for in vivo safety and efficacy, but also to understand the cellular controls underpinning glycan processing in a potential host cell (Grabenhorst et al., Glycoconjug. J., 16:81-97 (1999); James and Baker, Encyclopedia of bioprocess technology: Fermentation, biocatalysis and bioseparation. New York: John Wiley & Sons. p. 1336-1349 (1999)).

Just as with the eukaryotic cell chosen for the production of therapeutic recombinant glycoproteins, such as monoclonal antibodies, glycosylation is also highly dependent on the cell culture medium and other production process parameters (Ho et al., BioProcess International; 14(4):30-8 (2016)). Specifically, it has been shown that the composition of growth and feed media, including the concentrations of ammonia, glutamine, glucose, and metal ions, can influence antibody glycosylation (Hossler et al., Glycobiol. 19(9):936-946 (2009)). Accordingly, strategies have been developed to control the glycosylation pattern and/or profile of recombinant glycoproteins by supplementation of growth media. For example, WO2017079165 discloses supplementation with a fucose source, e.g. fucose, to cultures of cells engineered to lack GDP-keto-6-deoxymannose-3,5-epimerase, 4-reductase, or GDP-D-mannose-4,6-dehydratase activity to produce glycoproteins with a specific level of fucosylation. Fucose supplementation has been used to reduce afucosylated glycoforms, i.e. increase fucosylation, of antibodies, alone (WO2017120359; WO2017120347) or in combination with nicotinamide (WO2017134667). Manganese supplementation has been used to increase afucosylated glycoforms, i.e. to lower fucosylation, either alone (WO2017021871; WO2015011660; WO2013114245), in combination with copper (WO2016089919), or in combination with iron, copper, and zinc (WO2015128314). Manganese has also been used to control the galactosylation profile of the therapeutic monoclonal antibody Adalimumab (WO2012149197).

Thus, there is a need in the art for identification of methods that can predictably modify the glycosylation profile of recombinant glycoproteins of interest to better resemble that of a reference recombinant glycoprotein that meets all safety, efficacy, and regulatory standards.

SUMMARY OF THE INVENTION

The inventors found that the glycosylation profile of a recombinant glycoprotein produced in cell culture can be modified by a method comprising culturing eukaryotic cells expressing the recombinant glycoprotein in a cell culture medium supplemented with fucose, manganese, and taurine. The modification of the glycosylation profile by the inventive method is such that the glycosylation profile of the produced recombinant glycoprotein is modified to better resemble the glycosylation profile of a reference glycoprotein than when cultured without said supplementation.

The object of the present invention is solved by the subject matter of the independent claims. Preferred embodiments are apparent from the dependent claims.

Accordingly, in one embodiment the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose, manganese, and taurine, wherein the glycosylation profile of the produced recombinant glycoprotein is modified to better resemble the glycosylation profile of a reference glycoprotein than when cultured without said supplementation.

In an embodiment, the modified glycosylation profile comprises one or more of fucosylation profile and/or galactosylation profile. Preferably, the modified fucosylation profile is at least 90%, preferably at least 95%, more preferably at least 96%, more preferably at least 98% of the fucosylation profile of the reference glycoprotein and/or the modified galactosylation profile is at least 90%, preferably at least 95%, more preferably at least 96%, more preferably at least 98% of the galactosylation profile of the reference glycoprotein.

In an embodiment, the concentration of fucose in the culture medium is raised by between 0.4 mM and 1.6 mM, preferably between 0.4 mM and 1.2 mM, more preferably between 0.6 mM and 1 mM and preferably by 0.8 mM through supplementation.

In an embodiment, the concentration of manganese in the culture medium is raised by between 0.02 µM and 0.1 µM, preferably between 0.04 µM and 0.08 µM, more preferably between 0.06 µM and 0.08 µM, and most preferably by 0.068 µM±0.01 µM through supplementation.

In an embodiment, the final concentration of taurine in the culture medium after supplementation is between 12.5 mM and 50 mM, preferably between 15 mM and 35 mM, more preferably between 20 mM and 30 mM, and is preferably 25 mM.

In an embodiment, the method further comprises a step of isolating the produced recombinant glycoprotein from the cell culture.

In an embodiment, the eukaryotic cells are Chinese hamster ovary (CHO) cells.

In an embodiment, the recombinant glycoprotein is produced at large scale.

In an embodiment, the recombinant glycoprotein is an immunoglobulin of the IgG type.

In an embodiment, the recombinant glycoprotein is a monoclonal antibody, optionally a therapeutic monoclonal antibody.

In an embodiment, the cell culture occurs for 14 days.

In an embodiment, the supplementation of the culture medium occurs every 2nd day from a 3rd day of cultivation onwards, optionally until a 13th day of cultivation.

In an embodiment, the manganese is supplemented as manganese chloride ($MnCl_2$) and the supplementation of the culture medium with $MnCl_2$ occurs every 2nd day from a 5th day of cultivation onwards, optionally until a 9th day of cultivation.

In an embodiment, the supplementation of the culture medium occurs during the production phase of the cell culture.

In an embodiment, the cell culture occurs at 37° C.

In an embodiment, the cell culture occurs at pH 7.05±0.05.

In an embodiment, the cell culture is a fed-batch culture.

In an embodiment, the glycoprotein is a VEGF antagonist, preferably an anti-VEGF antibody. In this embodiment, the modified fucosylation profile preferably is at least 90%, preferably at least 95%, more preferably at least 96%, more preferably at least 98% of the fucosylation profile of the reference VEGF antagonist, preferably the anti-VEGF antibody and/or the modified galactosylation profile is at least 90%, preferably at least 95%, more preferably at least 96%, more preferably at least 98% of the galactosylation profile of the reference VEGF antagonist, preferably the anti-VEGF antibody.

In an embodiment, the glycoprotein is an anti-CD20 antibody. In this embodiment, the modified fucosylation profile preferably is at least 90%, preferably at least 95%, more preferably at least 96%, more preferably at least 98% of the fucosylation profile of the reference anti-CD20 antibody and/or the modified galactosylation profile is at least 90%, preferably at least 95%, more preferably at least 96%, more preferably at least 98% of the galactosylation profile of the reference anti-CD20 antibody.

DETAILED DESCRIPTION OF THE INVENTION

Figure 1:
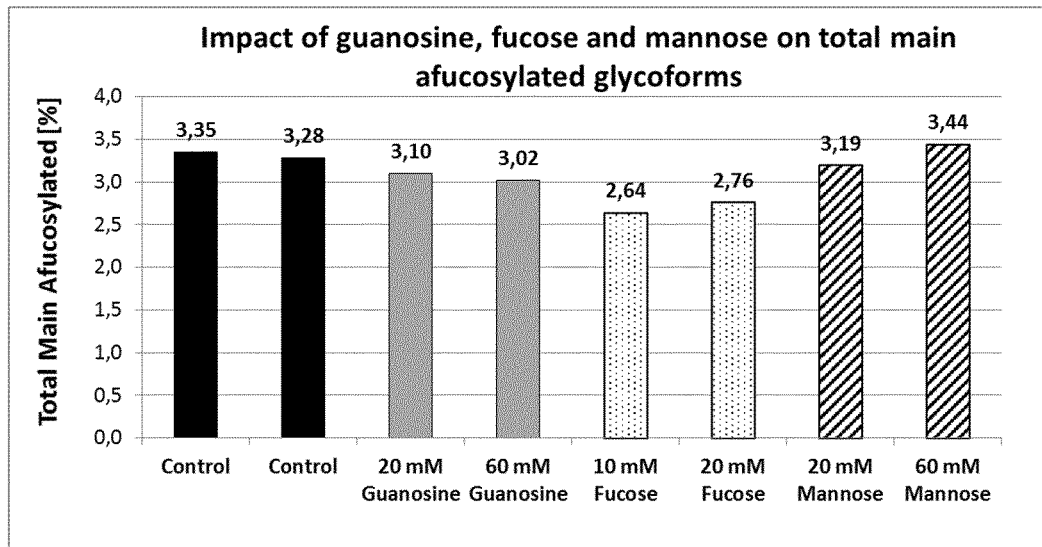
FIG. 1: Impact of guanosine, fucose and mannose on total main afucosylated (MAF) glycoforms of the anti-VEGF antibody of the present invention. Results are derived from day 12 of cultivation. Black bars: Control batches without culture medium additives. Grey bars: Batches fed with guanosine supplemented feed medium at two different concentrations (20 mM and 60 mM); Dotted bars: Batches fed with fucose supplemented feed medium at two different concentrations (10 mM and 20 mM); Diagonally striped bars: Batches fed with mannose supplemented feed medium at two different concentrations (20 mM and 60 mM).

The present invention, as illustratively described in the following, may suitably be practiced in the absence of any element or elements, limitation or limitations, not specifically disclosed herein.

The present invention will be described with respect to particular embodiments, but the invention is not limited thereto, but only by the claims.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

The term "polypeptide" or "protein" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If a discrete functional unit is comprised of more than one polypeptide that physically associate with one another, the term "protein" as used herein refers to the multiple polypeptides that are physically coupled and function together as the discrete unit.

The term "glycoprotein" is used herein to refer to a polypeptide or protein coupled to at least one carbohydrate moiety, e.g., a polysaccharide or an oligosaccharide, that is attached to the protein via an oxygen-containing or a nitrogen-containing side chain of an amino acid residue, e.g., a serine or threonine residue ("O-linked") or an asparagine residue ("N-linked"). "Glycoprotein" is used herein in the broadest sense and includes full-length glycoproteins, genetically engineered glycoproteins, recombinant glycoproteins, chimeric glycoproteins, humanized glycoproteins, fully human glycoproteins, as well as fragments of such glycoproteins, such as peptides, as long as they remain functional and exhibit the desired biological activity. The "biological activity" of a glycoprotein refers to the ability of the glycoprotein to elicit a biological response, which can be measured in vitro or in vivo.

The term "recombinant glycoprotein" refers to all glycoproteins prepared, expressed, created or isolated by recombinant means, such as glycoproteins isolated from a transgenic host cell, such as e.g. a NS0 or CHO cell, or from an animal transgenic for glycoprotein genes, or glycoproteins expressed using recombinant expression vectors transfected into a host cell, such as e.g. SP 2/0 mouse myeloma cells.

The term "glycan" refers to a polysaccharide or an oligosaccharide, e.g., a polymer comprised of monosaccharides. Glycans can be homo- or heteropolymers of monosaccharide residues, and can be linear or branched. Following the expression of proteins in eukaryotic, e.g. mammalian host cells, the proteins undergo post-translational modifications, often including the enzymatic addition of sugar residues, such as glycans. Such addition of sugar residues, e.g. glycans, is referred to herein as "glycosylation". "N-linked glycan" refers to a glycan attached to the side-chain of an asparagine residue. "O-linked glycan" refers to a glycan attached to a hydroxyamino acid, most commonly serine or threonine, although 5-hydroxyproline or 5-hydroxylysine may also be involved. Glycosylation includes, e.g., galactosylation and/or fucosylation.

As used herein, the "glycosylation pattern" of a recombinant glycoprotein of interest refers to various physical characteristics of the glycoprotein's polysaccharides or oligosaccharides, such as, e.g., the quantity and quality of various monosaccharides present, the degree of branching, and/or the attachment (e.g., N-linked or O-linked). The "glycosylation pattern" of a glycoprotein can also refer to the functional characteristics imparted by the glycoprotein's oligosaccharides and polysaccharides. For example, the extent to which the glycoprotein can bind to FcγRIIIa and induce antibody-dependent cellular cytotoxicity (ADCC).

As used herein, the "glycosylation profile" or "glycosylation degree" of a recombinant glycoprotein of interest refers to the quantity of various monosaccharides present. The glycosylation profile may vary between differently produced batches of a glycoprotein of interest, e.g. between a biosimilar therapeutic glycoprotein and its reference product glycoprotein. While some degree of variation in glycosylation profile may be allowable within regulatory standards without necessitating new clinical trials for approval of a therapeutic glycoprotein biosimilar, it is most desirable to match the glycosylation profile of the reference glycoprotein as closely as possible, thereby also maintaining safety and efficacy at levels as close as possible to those of the reference glycoprotein. The glycosylation profile of a recombinant glycoprotein may comprise, e.g., the fucosylation profile and/or the galactosylation profile of the recombinant glycoprotein.

The term "fucosylation" refers to the degree and distribution of fucose residues on polysaccharides and oligosaccharides, for example, N-glycans, O-glycans and glycolipids. The term "fucosylation profile" or "fucosylation degree" refers to the quantity of fucose residues on polysaccharides and oligosaccharides, for example N-glycans, O-glycans, and glycolipids. Therapeutic glycoproteins, e.g., antibodies or Fc fusion proteins, with non-fucosylated, or "afucosylated" N-glycans exhibit dramatically enhanced antibody-dependent cellular cytotoxicity (ADCC) due to the enhancement of FcγRIIIa binding capacity without any detectable change in complement-dependent cytotoxicity (CDC) or antigen binding capability. In certain situations, e.g., cancer treatment, non-fucosylated or "afucosylated" antibodies, i.e. antibodies with a low "fucosylation profile", are desirable because they can achieve therapeutic efficacy at low doses, while inducing high cellular cytotoxicity against tumor cells, and triggering high effector function in natural killer (NK) cells via enhanced interaction with FcγRIIIa. In other situations, e.g., treatment of inflammatory or autoimmune diseases, enhanced ADCC and FcγRIIIa binding is not desirable, and accordingly, therapeutic glycoproteins with higher levels of fucose residues, i.e. a higher fucosylation profile, in their N-glycans can be preferable. The fucosylation profile may vary between differently produced batches of a glycoprotein of interest, e.g. between a biosimilar therapeutic glycoprotein and its reference product glycoprotein. While some degree of variation in fucosylation profile may be allowable within regulatory standards without necessitating new clinical trials for approval of a therapeutic glycoprotein biosimilar, it is most desirable to match the fucosylation profile as closely as possible to that of the reference glycoprotein, thereby also maintaining safety and efficacy at levels as close as possible to those of the reference glycoprotein.

"Galactosylation" refers to the type and distribution of galactose residues on polysaccharides and oligosaccharides, for example, N-glycans, O-glycans and glycolipids. The term "galactosylation profile" or "galactosylation degree" refers to the quantity of galactose residues on polysaccharides and oligosaccharides, for example N-glycans, O-glycans, and glycolipids. "Galactose" refers to a group of monosaccharides, which include open chain and cyclic forms. An important disaccharide form of galactose is galactose-alpha-1,3-galactose (a-gal). The galactosylation profile may vary between differently produced batches of a glycoprotein of interest, e.g. between a biosimilar therapeutic glycoprotein and its reference product glycoprotein. While some degree of variation in galactosylation profile may be allowable within regulatory standards without necessitating new clinical trials for approval of a therapeutic glycoprotein biosimilar, it is most desirable to match the galactosylation profile as closely as possible to that of the reference glycoprotein, thereby also maintaining safety and efficacy at levels as close as possible to those of the reference glycoprotein.

The terms "modifying the glycosylation profile", "modifying the fucosylation profile", and "modifying the galactosylation profile" refer to a change in the glycosylation profile, fucosylation profile, and galactosylation profile, respectively, of a recombinant glycoprotein when it is produced under a first set of culture conditions, e.g. in the presence of fucose, manganese, and/or taurine in the cell culture medium, as compared to the glycosylation profile, fucosylation profile, and galactosylation profile, respectively, of the same recombinant glycoprotein when it is produced under a second set of culture conditions, e.g. in the absence of fucose, manganese, and/or taurine in the cell culture medium. The glycosylation profile, fucosylation profile, and/or galactosylation profile achieved under the first set of culture conditions may be increased or decreased relative to the profile achieved under the second set of culture conditions. Preferably, the glycosylation profile, fucosylation profile, and/or galactosylation profile achieved by the first set of culture conditions is modified to better resemble the glycosylation profile, fucosylation profile, and/or galactosylation profile, respectively, of a reference glycoprotein than the glycosylation profile, fucosylation profile, and/or galactosylation profile, respectively, achieved under the second set of culture conditions. More preferably, the glycosylation profile, fucosylation profile, and/or galactosylation profile is modified to be at least 90%, still more preferably at least 95%, more preferably at least 96%, most preferably at least 98% of the glycosylation profile, fucosylation profile, and/or galactosylation profile, respectively, of the reference glycoprotein.

The term "reference glycoprotein", "reference VEGF antagonist", "reference anti-VEGF antibody" or "reference anti-CD20 antibody" as used herein refers to the same glycoprotein, antagonist, or antibody of interest as is being produced in the relevant cell culture, which it is desirable to match or to better resemble in terms of the glycosylation profile, fucosylation profile, and/or galactosylation profile of the glycoprotein of interest. For example, the reference glycoprotein, antagonist, or antibody may have useful properties, such as stability, efficacy, safety, and/or other properties that are relevant for a given glycoprotein, antagonist, or antibody. A reference glycoprotein, antagonist, or antibody may, for example, be a glycoprotein, antagonist, or antibody that has gained regulatory approval for therapeutic use in a subject, e.g. a human subject. In this case, the glycoprotein being produced in the method of modifying the glycosylation profile, fucosylation profile, and/or galactosylation profile may be a biosimilar.

The terms "culture", "cell culture" and "eukaryotic cell culture" as used herein refer to a eukaryotic cell population, either surface-attached or in suspension, that is maintained or grown in a cell culture medium under conditions suitable to survival and/or growth of the cell population. These terms, as used herein, can refer to the combination comprising the mammalian cell population and the cell culture medium in which the population is suspended. Cell cultures can be, e.g., continuous cultures, batch cultures, fed-batch cultures, or other culture types.

The terms "media", "medium", "cell culture medium", "culture medium", "tissue culture medium", "tissue culture media", and "growth medium" as used herein refer to a solution containing nutrients, which support growth of cultured eukaryotic cells. Typically, these solutions provide essential and non-essential amino acids, vitamins, energy sources, lipids, and trace elements required by the cell for minimal growth and/or survival. The solution can also contain components that enhance growth and/or survival above the minimal rate, including hormones and growth factors. The solution is formulated to a pH and salt concentration optimal for cell survival and proliferation. The medium can also be a "defined medium" or "chemically defined medium", a serum-free medium that contains no proteins, hydrolysates or components of unknown composition. Defined media are free of animal-derived components and all components have a known chemical structure. A defined medium can comprise recombinant glycoproteins or proteins, for example, but not limited to, hormones, cytokines, interleukins and other signalling molecules.

The cell culture medium is generally "serum-free" when the medium is essentially free of serum, or fractions thereof, from any mammalian source (e.g. essentially free of fetal bovine serum (FBS)). By "essentially free" is meant that the cell culture medium comprises between about 0-5% serum, preferably between about 0-1% serum, and most preferably between about 0-0.1% serum. Advantageously, serum-free defined medium can be used, wherein the identity and concentration of each of the components in the medium is known (i.e., an undefined component, such as an extract of eukaryotic cells, is not present in the culture medium).

The cell culture of the present invention is performed in any medium suitable for the particular cell being cultured. In some embodiments, the medium contains e.g., inorganic salts, carbohydrates (e.g., sugars such as glucose, galactose, maltose or fructose), amino acids, vitamins (e.g., B group vitamins (e.g., B12), vitamin A, vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), and combinations thereof. Commercially available media such as 5x-concentrated DMEM/F12 (Invitrogen), CD OptiCHO feed (Invitrogen), CD EfficientFeed (Invitrogen), Cell Boost (HyClone), BalanCD CHO Feed (Irvine Scientific), BD Recharge (Becton Dickinson), Cellvento Feed (EMD Millipore), Ex-cell CHOZN Feed (Sigma-Aldrich), CHO Feed Bioreactor Supplement (Sigma-Aldrich), ShffCHO (Kerry), Zap-CHO (Invitria), ActiCHO (PAA/GE Healthcare), Ham's F10 (Sigma), Minimal Essential Medium ([MEM], Sigma), RPMI-1640 (Sigma), and Dulbecco's Modified Eagle's Medium ([DMEM], Sigma) are exemplary cell culture media suitable for the method of the present invention. In addition, any of the media described in Ham and Wallace, (1979) Meth. Enz., 58:44; Barnes and Sato, (1980) Anal. Biochem., 102:255; U.S. Pat. Nos. 4,767,704; 4,657,866; 4,927,762; 5,122,469 or 4,560,655; International Publication Nos. WO 90/03430; and WO 87/00195; can be used as culture media. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range), lipids (such as linoleic or other fatty acids) and their suitable carriers, and glucose or an equivalent energy source. In some embodiments the culture medium is a serum-free medium, a protein-free medium, or a chemically defined medium. Any other necessary supplements can also be included at appropriate concentrations that would be known to those skilled in the art.

The term "basal media formulation", "basal medium", or "basal media" as used herein refers to any cell culture medium used to culture cells that has not been modified, either by supplementation with, or by selective removal of, a certain component or certain components.

The term "feed medium", "feed media", or "feed" as used herein refers to any cell culture medium added after the beginning of a cell culture. It is often more highly concentrated than a cell culture medium used at the start of a cell culture and serves to restock used up nutrients or to supply supplements or additives to the cell culture.

The terms "supplementation", "supplementing" or "supplemented" refer to the addition of an additive or supplement to a cell culture medium, e.g. a basal medium or a feed medium. As used herein, the terms "additive" or "supplement" refer to any supplementation made to a basal medium or a feed medium to achieve the goals described in this disclosure. An additive or supplement can include a single substance, e.g. taurine, manganese, or fucose, or can include multiple substances, e.g., fucose and taurine, fucose and manganese, taurine and manganese, or fucose, manganese and taurine. The terms "additive" or "supplement" refer to all of the components added, even though they need not be added at the same time, and they need not be added in the same way. For example, one or more components of an additive or supplement can be added as a single bolus or two or more boli from a stock solution, while other components of the same additive or supplement can be added as part of a feed medium. Addition of the supplement(s) can also occur continuously or semi-continuously. In addition, any one or more components of an additive or supplement can be present in the basal medium from the beginning of the cell culture. Supplementation can thus occur at the beginning of a culture, and/or subsequent to the beginning of a culture, e.g. during the growth phase and/or the production phase.

The term "raise by" or "raised by" as used herein means that a concentration of an additive or supplement before supplementation with said supplement is increased through supplementation to a higher concentration of that supplement or additive after supplementation. That is, the cell culture medium being supplemented has a concentration of the supplement or additive that is higher by the defined amount after compared to before supplementation with the supplement or additive.

The term "growth phase" of the cell culture refers to the period of exponential cell growth (the log phase) where cells are generally rapidly dividing. The determination of the growth cycle for the cells of the cell culture can be determined for the particular cell envisioned without undue experimentation. During the growth phase, cells are cultured in cell culture medium containing the necessary additives, generally at about 25°-40° C., preferably at 37° C., in a controlled atmosphere, such that optimal growth is achieved for the particular cells, e.g. cells of a cell line. Cells are maintained in the exponential growth phase for a period of about between one and five days, e.g., between two to four days, e.g., four days. For example, the length of the growth phase will be the period of time sufficient to allow the particular cells to reproduce to a viable cell density within a range of about 20%-80% of the maximally possible viable cell density if the culture was maintained under the growth conditions of the invention/as outlined above.

"Production phase" or "protein production phase" of the cell culture refers to the period of time when cell growth has reached a stationary phase. During the production phase, logarithmic cell growth has ended and protein production is the primary activity in the cell culture. During this period of time the medium is generally supplemented to support continued protein production and to achieve the desired glycoprotein product. The production phase typically starts at day 5 of cultivation and lasts until the end of cultivation, preferably until day 14 of cultivation.

The term "cell viability" as used herein refers to the ability of cells in culture to survive under a given set of culture conditions or experimental variations. The term as used herein also refers to that portion of cells, which are alive at a particular time in relation to the total number of cells, living and dead, in the culture at that time. The term "cell density" or "viable cell density" as used herein refers to that number of living cells present in a given volume of medium.

The term "batch culture" as used herein refers to a method of culturing cells in which all the components that will ultimately be used in culturing the cells, including the medium, as well as the cells themselves, are provided at the beginning of the culturing process. A batch culture is typically stopped at some point and the cells and/or components in the medium are harvested and optionally purified.

The term "fed-batch culture" as used herein refers to a method of culturing cells in which additional components are provided to the culture at some time subsequent to the beginning of the culture process. A fed-batch culture can be started using, e.g., a basal medium. The culture medium with which additional components are provided to the culture at some time subsequent to the beginning of the culture process is a "feed medium" or a "feed solution". A fed-batch culture is typically stopped at some point and the cells and/or components in the medium are harvested and optionally purified.

The term "continuous culture" or "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified.

Cell culture typically occurs in a bioreactor. The term "bioreactor" as used herein refers to any vessel used for the growth of a mammalian cell culture. Depending on the scale of the culture, the bioreactor can be of any size so long as it is useful for the culturing of mammalian cells. Typically, the bioreactor will be at least 500 milliliters and can be 1, 10, 50, 100, 250, 500, 1,000, 2,000, 2,500, 3,000, 5,000, 8,000, 10,000, 12,0000, 15,000, 20,000 liters or more, or any volume in between. For example, a bioreactor will be 10 to 5,000 liters, 10 to 10,000 liters, 10 to 15,000 liters, 10 to 20,000 liters, 50 to 5,000 liters, 50 to 10,000 liters, 50 to 15,000 liters, 50 to 20,000 liters, 1,000 to 5,000 liters, or 1,000 to 3,000 liters. A bioreactor can be a stirred-tank bioreactor or a shake flask. The internal conditions of the bioreactor, including e.g. pH and temperature, are typically tightly controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the glycoprotein or protein of interest.

The term "large-scale cell culture" or "large-scale production" as used herein refers to cell cultures in a production bioreactor with a volume of, typically, at least 500 or 1,000 liters, preferably at least 5,000 or 8,000 liters and most preferably of 10,000 or 20,000 liters.

The term "antibody" or "immunoglobulin" is used herein interchangeably and in the broadest sense and includes full-length antibodies, genetically engineered antibodies, recombinant antibodies, multivalent antibodies, monoclonal antibodies, polyclonal antibodies, bispecific antibodies, multispecific antibodies, chimeric antibodies, humanized antibodies, fully human antibodies, as well as fragments of such antibodies as long as they remain biologically functional and exhibit the desired biological activity. The "biological activity" of an antibody refers to the ability of the antibody to bind to antigen and results in a biological response, which can be measured in vitro or in vivo.

Naturally occurring antibodies are molecules with varying structures. For example, native IgG antibodies are heterotetrameric glycoproteins of about 150,000 Daltons, composed of two identical light chains and two identical heavy chains that are linked by disulfide bonds. From N- to C-terminus, each heavy chain has a variable domain ($V_H$), also called a variable heavy domain or a heavy chain variable domain, followed by three or four constant domains ($C_H1$, $C_H2$, $C_H3$ and optionally $C_H4$). Similarly, from N- to C-terminus, each light chain has a variable domain ($V_L$), also called a variable light domain or a light chain variable domain, followed by a constant light chain ($C_L$) domain. The light chain of an antibody may be assigned to one of two types, called kappa (κ) and lambda (λ), based on the amino acid sequence of its constant domain.

A "full-length antibody" comprises an antigen-binding variable region of the light ($V_L$) and heavy chain ($V_H$), a light chain constant region (CO and heavy chain constant domains $C_H1$, $C_H2$ and $C_H3$.

The term "antibody fragment" or "antigen-binding fragment" is used herein in the broadest sense and comprises a portion of a full-length antibody, preferably comprising the antigen-binding or variable region thereof. An antibody fragment retains the original specificity of the parent immunoglobulin. Examples of antibody fragments include, e.g., Fab, Fab', $F(ab)_2$, and Fv fragments, diabodies, linear antibodies, single-chain antibody molecules, and multispecific antibodies formed from antibody fragment(s). Preferably, the antibody fragment is a Fab fragment.

A "monoclonal antibody" is an antibody that is specific for a single epitope of an antigen, i.e. directed against a single determinant on an antigen. Methods for producing monoclonal antibodies are known to the person skilled in the art.

The term "recombinant antibody" refers to all antibodies prepared, expressed, created or isolated by recombinant means, such as antibodies isolated from a transgenic host cell, such as e.g. a NS0 or CHO cell, or from an animal transgenic for immunoglobulin genes, or antibodies expressed using recombinant expression vectors transfected into a host cell, such as e.g. SP 2/0 mouse myeloma cells.

The antibody or immunoglobulin of the invention is preferably an IgG molecule, such as an IgG1, IgG2, IgG3, or IgG4 molecule. More preferably, the immunoglobulin is IgG1. Even more preferably, the immunoglobulin is an IgG1 wherein at least the Fc part is human.

A "chimeric antibody", e.g. a murine-human chimeric antibody is an antibody wherein the Fc part is human and the variable region is of mouse origin.

In one embodiment of the invention, the chimeric antibody is rituximab or infliximab.

Rituximab is a chimeric anti-CD20 antibody, which is described in detail in, for example, WO 94/11026.

Infliximab is a chimeric anti-TNFa antibody, which is described in detail in, for example, WO 92/16553.

A "humanized antibody" is a human antibody wherein the antigen binding portion (complementarity-determining region (CDR)) is derived from non-human species, such as a mouse, and thus has a different specificity compared to the parent immunoglobulin. The CDR protein sequences can be modified to increase their similarities to antibody variants produced naturally in humans.

In one embodiment of the invention, the humanized antibody is trastuzumab or bevacizumab.

Trastuzumab is a humanized anti-HER2 antibody, which is described in detail in, for example, WO 92/22653.

Bevacizumab is a humanized anti-VEGF antibody, which is described in detail in, for example, WO 98/45331.

A "fully human antibody" is an antibody in which all parts are derived from human origin.

In one embodiment of the invention, the human antibody is adalimumab or denosumab.

Adalimumab is a human anti-TNFa antibody, which is described in detail in, for example, WO 97/29131.

Denosumab is a human anti-RANKL antibody, which is described in detail in, for example, WO 03/002713.

In a preferred embodiment, the antibody is rituximab or bevacizumab.

The term "therapeutic antibody" refers to an antibody that is used in the treatment of a disease. A therapeutic antibody may have various mechanisms of action. A therapeutic antibody may bind and neutralize the normal function of a target associated with an antigen. For example, a monoclonal antibody that blocks the activity of proteins needed for the survival of a cancer cell causes the cell's death. Another therapeutic monoclonal antibody may bind and activate the normal function of a target associated with an antigen. For example, a monoclonal antibody can bind to a protein on a cell and trigger an apoptosis signal. Yet another monoclonal antibody may bind to a target antigen expressed only on diseased tissue; conjugation of a toxic payload (effective agent), such as a chemotherapeutic or radioactive agent, to the monoclonal antibody can create an agent for specific delivery of the toxic payload to the diseased tissue, reducing harm to healthy tissue. A "biologically functional fragment" of a therapeutic antibody will exhibit at least one if not some or all of the biological functions attributed to the intact antibody, the function comprising at least specific binding to the target antigen.

The term "osmolality" is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of water (1 mOsm/kg $H_2O$ at 37° C. is equivalent to an osmotic pressure of 2.5 kPA (19 mm Hg)). The osmolality of a culture increases over the cell culture period and/or when additional solute particles are added, e.g. as a supplement, unless it is modulated and/or stabilized. Accordingly, the longer a cell culture period, the higher the osmolality.

"Osmolarity" refers to the number of solute particles dissolved in 1 liter of solution. Accordingly, addition of solutes, such as supplements, e.g. fucose, manganese, and/or taurine, to the culture medium will increase the osmolarity thereof. Typically, a given cell culture will require an optimal osmolarity range of the cell culture medium, and the osmolality accordingly must be kept stably within that optimal osmolarity range. When used herein, the abbreviation "mOsm" means "milliosmoles/kg $H_2O$".

The term "titer" as used herein refers to the total amount of recombinantly expressed glycoprotein produced by a cell culture divided by a given amount of medium volume. Titer is typically expressed in units of milligrams of glycoprotein per milliliter of medium or in units of grams of glycoprotein per liter of medium.

The terms "isolating", "isolate", "isolated", "purify", "purifying", and "purified" as used herein refer to the removal or separation of some or all of the cells, cell debris, cell culture medium, components of the cell culture medium, and other materials making up the cell culture in which the recombinant glycoprotein was produced from the recombinant glycoprotein. In general, it will typically be desirable to isolate the glycoproteins produced in the cell culture. The glycoprotein may, e.g., be secreted into the medium and thus cells and other solids can be removed, e.g. by centrifugation or filtering, as a first step in the isolation process. Alternatively, the expressed glycoprotein may be bound to the surface of the cells of the cell culture. In this embodiment, the media is removed and the cells expressing the glycoprotein are lysed as a first step in the purification process. Lysis of mammalian cells can be achieved by any number of means well known to those of ordinary skill in the art, including physical disruption by glass beads and exposure to high pH conditions. The glycoprotein can be isolated and/or purified by standard methods including, e.g., chromatography (e.g., ion exchange, affinity, size exclusion, and hydroxyapatite chromatography), gel filtration, centrifugation, differential solubility, ethanol precipitation, or by any other available technique for the purification of proteins (see, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997). For immunoaffinity chromatography in particular, the glycoprotein can be isolated by binding it to an affinity column comprising antibodies that were raised against that protein and were affixed to a stationary support. Alternatively, affinity tags such as, e.g., an influenza coat sequence, poly-histidine, or glutathione-S-transferase can be attached to the glycoprotein by standard recombinant techniques to allow for easy purification by passage over the appropriate affinity column. Protease inhibitors such as phenyl methyl sulfonyl fluoride (PMSF), leupeptin, pepstatin or aprotinin can be added at any or all stages in order to reduce or eliminate degradation of the glycoprotein during the isolation and/or purification process. Protease inhibitors are particularly desired when cells must be lysed in order to isolate and purify the expressed glycoprotein. One of ordinary skill in the art will appreciate that the exact isolation and/or purification technique will vary depending on the character of the glycoprotein to be isolated and/or purified, the character of the cells from which the glycoprotein is expressed, and the composition of the medium in which the cells were grown.

Where it is desirable to modulate the glycosylation profile, e.g. to reduce the amount of afucosylated glycoforms of a recombinant glycoprotein produced in cell culture, e.g. to reduce ADCC of the glycoprotein and/or to produce a glycoprotein with a fucosylation profile similar to a reference glycoprotein, fucose may be supplemented to the cell culture (see Example 2). However, addition of fucose can also lead to decreases in the galactosylation profile of the produced glycoprotein, which in turn may result in a glycosylation and/or galactosylation profile that is undesirable because it is not similar to the glycosylation and/or galactosylation profile of the reference glycoprotein, and/or in terms of biological activity, safety and/or efficacy of the produced glycoprotein (see also Raju and Jordan. MAbs. May 1; 4(3): 385-391 (2012)).

As a countermeasure to the decrease in galactosylation manganese may further be supplemented during cell culture. While this additional supplementation of manganese alters the galactosylation profile of the produced glycoprotein such that no decrease as observed with only fucose supplementation is caused, i.e. that the galactosylation profile is similar to/better resembles that of the reference glycoprotein, it also leads/adds to an increase in osmolality of the culture. This increase in osmolality, on top of the relatively high osmolality caused by long durations of the cell culture to increase the amount of produced glycoprotein, e.g. a duration of 11-18 days, e.g. of 13-15 days, e.g. of 14 days, in turn, increases the formation of afucosylated glycoforms, i.e. it leads to a decrease in the fucosylation profile, of the glycoprotein (see Example 3). This of course is exactly the opposite of the effect that is to be achieved by the initial supplementation with fucose, and is in contrast to observations previously made in the art, where higher osmolality, irrespective of the responsible solute, led to a decrease in afucosylated glycoforms, i.e. an increase in fucosylated glycoforms (Konno et al., Cytotechnology 64(3):249-65 (2012)).

To counteract this undesirable increase in afucosylated glycoforms observed upon supplementation of the cell culture with fucose and manganese, further supplementation with taurine as an osmoprotectant was attempted (see Example 4). Surprisingly, it was found that taurine can not only serve to stabilize the osmolality of a cell culture, but also to further decrease the formation of afucosylated glycoforms, i.e. to increase the fucosylation profile, of the produced glycoprotein (see Example 5). Thereby, supplementation of a cell culture medium with fucose, manganese, and taurine can alter the glycosylation profile, including the fucosylation and/or galactosylation profile, of a glycoprotein produced in cell culture to better resemble that of a reference glycoprotein than when no supplementation occurs. Using taurine as opposed to osmoprotectants commonly used in the art, such as betaine, has the additional benefit of also increasing the production titer (WO2017024062).

Accordingly, in one embodiment, the present invention provides a method of modifying the glycosylation profile, comprising one or more of fucosylation profile and/or galactosylation profile, of a recombinant glycoprotein produced in cell culture comprising culturing eukaryotic cells expressing the recombinant glycoprotein in a cell culture medium, and wherein the cell culture medium is supplemented with fucose, manganese, and taurine, wherein the glycosylation profile, comprising one or more of fucosylation profile and/or galactosylation profile, of the produced recombinant glycoprotein is modified to better resemble the glycosylation profile, comprising one or more of fucosylation profile and/or galactosylation profile, of a reference glycoprotein than when cultured without said supplementation.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose, manganese, and taurine, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein. Preferably, the modified fucosylation profile is at least 98% of the fucosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose, manganese, and taurine, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose, manganese, and taurine, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In an embodiment, the concentration of fucose in the culture medium is raised by between 0.4 mM and 1.6 mM, for example 0.4, 0.44, 0.48, 0.52, 0.56, 0.6, 0.64, 0.68, 0.72, 0.76, 0.8, 0.84, 0.88, 0.92, 0.96, 1, 1.04, 1.08, 1.12, 1.16, 1.2, 1.24, 1.28, 1.32, 1.36, 1.4, 1.44, 1.48, 1.52, 1.56, or 1.6 mM through supplementation. In a preferred embodiment, the concentration of fucose in the culture medium is raised by between 0.4 mM and 1.2 mM, for example 0.4, 0.44, 0.48, 0.52, 0.56, 0.6, 0.64, 0.68, 0.72, 0.76, 0.8, 0.84, 0.88, 0.92, 0.96, 1, 1.04, 1.08, 1.12, 1.16, or 1.2 mM through supplementation. In a preferred embodiment, the concentration of fucose in the culture medium is raised by between 0.6 mM and 1 mM, for example 0.6, 0.64, 0.68, 0.72, 0.76, 0.8, 0.84, 0.88, 0.92, 0.96, or 1 mM through supplementation. In a most preferred embodiment, the concentration of fucose in the culture medium is raised by 0.8 mM through supplementation Preferably, supplementation with fucose as described above is achieved by supplementation as part of a feed medium, wherein the concentration of fucose in the feed medium is between 10 mM and 40 mM, for example 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mM. In a preferred embodiment, the concentration of fucose in the feed medium is between 10 mM and 30 mM, for example 10, 11, 12, 13, 14, 15, 16, 17, 18, 19, 20, 21, 22, 23, 24, 25, 26, 27, 28, 29, or 30 mM. In a preferred embodiment, the concentration of fucose in the feed medium is between 15 mM and 25 mM, for example 15, 16, 17, 18, 19, 20, 21, 22, 23, 24, or 25 mM. In a most preferred embodiment, the concentration of fucose in the feed medium is 20 mM.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, more preferably by 0.4 to 1.2 mM, yet more preferably by 0.6 to 1 mM, most preferably by 0.8 mM, manganese, and taurine, and wherein the glycosylation profile of the produced recombinant glycoprotein is modified to better resemble the glycosylation profile of a reference glycoprotein than when cultured without said supplementation.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, more preferably by 0.4 to 1.2 mM, yet more preferably by 0.6 to 1 mM, most preferably by 0.8 mM, manganese, and taurine, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, more preferably by 0.4 to 1.2 mM, yet more preferably by 0.6 to 1 mM, most preferably by 0.8 mM, manganese, and taurine, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, more preferably by 0.4 to 1.2 mM, yet more preferably by 0.6 to 1 mM, most preferably by 0.8 mM, manganese, and taurine, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In an embodiment, the concentration of manganese in the culture medium is raised by between 0.02 µM and 0.1 µM, preferably between 0.04 µM and 0.08 µM, more preferably between 0.06 µM and 0.08 µM, and most preferably by 0.068 µM±0.01 µM.

Preferably, supplementation with manganese as described above is achieved by supplementation as part of a feed medium, wherein the concentration of manganese in the feed medium is between 0.5 µM to 2.5 µM, preferably of 1.0 µM to 2.0 µM, more preferably of 1.5 µM to 2.0 µM, and most preferably of 1.7 µM±0.2 µM.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM and taurine, and wherein the glycosylation profile of the produced recombinant glycoprotein is modified to better resemble the glycosylation profile of a reference glycoprotein than when cultured without said supplementation.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.02 µM to 0.1 µM, preferably by 0.04 µM to 0.08 µM, more preferably by 0.06 µM to 0.08 µM, and most preferably of 0.068 µM±0.01 µM, and taurine, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the glycosylation profile of the produced recombinant glycoprotein is modified to better resemble the glycosylation profile of a reference glycoprotein than when cultured without said supplementation.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the glycosylation profile of the produced recombinant glycoprotein is modified to better resemble the glycosylation profile of a reference glycoprotein than when cultured without said supplementation.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.02 µM to 0.1 µM, preferably by 0.04 µM to 0.08 µM, more preferably by 0.06 µM to 0.08 µM, and most preferably by 0.068 µM±0.01 µM, and taurine, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In an embodiment, the concentration of taurine in the culture medium after supplementation is between 12.5 mM and 50 mM, for example 12.5, 15, 17.5, 20, 22.5, 25, 27.5, 30, 32.5, 35, 37.5, 40, 42.5, or 50 mM. In a preferred embodiment, the final concentration of taurine in the culture medium after supplementation is between 15 mM and 35 mM, for example 15, 17.5, 20, 22.5, 25, 27.5, 30, 32.5, or 35 mM. In a preferred embodiment, the final concentration of taurine in the culture medium after supplementation is between 20 mM and 30 mM, for example 20, 22.5, 25, 27.5, or 30 mM. In a most preferred embodiment, the final concentration of taurine in the culture medium after supplementation is 25 mM.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose, manganese, and taurine at a final concentration of 12.5 to 50 mM in the cell culture medium after supplementation, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose, manganese, and taurine at a concentration in the culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose, manganese, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose, manganese, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese, and taurine at a final concentration in the cell culture medium after supplementation of 12.5 to 50 mM, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein than when cultured without said supplementation.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese, and taurine at a final concentration in the cell culture medium after supplementation of 12.5 to 50 mM, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein than when cultured without said supplementation.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble to the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein than when cultured without said supplementation.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble the fucosylation profile of a reference glycoprotein than when cultured without said supplementation.

Preferably, the modified fucosylation profile is at least 90%, preferably at least 95%, more preferably at least 96%, more preferably at least 98% of the fucosylation profile of the reference glycoprotein.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose, manganese so that concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein than when cultured without said supplementation.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein than when cultured without said supplementation.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein than when cultured without said supplementation.

In one embodiment, the present invention provides a method of modifying the glycosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the glycosylation profile of the produced recombinant glycoprotein is modified to better resemble the glycosylation profile of a reference glycoprotein than when cultured without said supplementation.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble the fucosylation profile of a reference glycoprotein than when cultured without said supplementation.

Preferably, the modified fucosylation profile is at least 90%, preferably at least 95%, more preferably at least 96%, more preferably at least 98% of the fucosylation profile of the reference glycoprotein.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 20 mM, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In one embodiment, the present invention provides a method of modifying the fucosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile of the produced recombinant glycoprotein is modified to better resemble the fucosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In another embodiment, the present invention provides a method of modifying the galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the galactosylation profile of the produced recombinant glycoprotein is modified to better resemble the galactosylation profile of a reference glycoprotein than when cultured without said supplementation. Preferably, the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.6 mM, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.06 µM to 0.08 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.4 to 1.4 mM, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In yet another, preferred, embodiment, the present invention provides a method of modifying the fucosylation profile and galactosylation profile of a recombinant glycoprotein produced in cell culture comprising culturing eukaryotic cells expressing the recombinant glycoprotein in a cell culture medium, wherein the cell culture medium is supplemented with fucose so that the concentration of fucose in the cell culture medium is raised by 0.8 mM, manganese so that the concentration of manganese in the cell culture medium is raised by 0.068 µM±0.01 µM, and taurine at a final concentration in the cell culture medium after supplementation of 12.5 to 50 mM, more preferably of 15 to 35 mM, yet more preferably of 20 to 30 mM, most preferably of 25 mM, and wherein the fucosylation profile and galactosylation profile of the produced recombinant glycoprotein are modified to better resemble the fucosylation profile and galactosylation profile of a reference glycoprotein than when cultured without said supplementation. Preferably, the modified fucosylation profile is at least 90%, preferably at least 95%, more preferably at least 96%, more preferably at least 98% of the fucosylation profile of the reference glycoprotein and the modified galactosylation profile is at least 90%, preferably at least 95%, more preferably at least 96%, more preferably at least 98% of the galactosylation profile of the reference glycoprotein.

In an embodiment, the method of any one of the previous embodiments further comprises a step of isolating the produced recombinant glycoprotein from the cell culture. In a specific embodiment, the isolation step comprises Protein A purification.

Any eukaryotic cell or cell type susceptible to cell culture and capable of expressing a recombinant glycoprotein can be utilized in accordance with the present invention and in particular with any one of the previous embodiments of the invention. For example, plant cells, yeast cells, animal cells, insect cells, avian cells or mammalian cells can be utilized in accordance with the present invention. Examples of mammalian cells that can be used in accordance with the present invention include BALB/c mouse myeloma line (NS0/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells±DHFR (CHO, Urlaub and Chasin, Proc. Natl. Acad. Sci. USA, 77:4216 (1980)), e.g., Chinese hamster ovary cell line M (CHO-M); mouse Sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCLS 1); TRI cells (Mather et al, Annals N. Y. Acad. Sci., 383:44-68 (1982)); MRC 5 cells; and FS4 cells.

The eukaryotic cells suitable for the present invention can be selected or engineered to produce high levels of glycoprotein. Often, cells are genetically engineered to produce high levels of glycoprotein, for example by introduction of a gene encoding the recombinant glycoprotein of interest and/or by introduction of control elements that regulate expression of the gene (whether endogenous or introduced) encoding the recombinant glycoprotein of interest.

The eukaryotic cells can also or alternatively be selected or engineered to allow culturing in serum free medium.

In an embodiment, the eukaryotic cells comprise a vector comprising a polynucleotide encoding a protein that is later glycosylated.

In another embodiment, a commercially or non-commercially available hybridoma cell line that expresses at least one glycoprotein can be utilized in accordance with the present invention. In a preferred embodiment, the eukaryotic cells are Chinese hamster ovary (CHO) cells. In a preferred embodiment, the CHO cells comprise a vector comprising a polynucleotide encoding a protein that is later glycosylated. For example, CHO-K1 (ATCC CCL-61), CHO-DUKX (ATCC CRL-9096), Lec1 ATCC CRL-1735, CHO-DG44 (ThermoFisher), CHO-M (Selexis), CHO-S (ThermoFisher) or CHO Pro-5 (ATCC CRL-1781) are suitable.

In an especially preferred embodiment, the eukaryotic cells are of the Selexis SURE CHO-M Cell Line (CHO-M). In a preferred embodiment, the CHO-M cells comprise a vector comprising a polynucleotide encoding a protein that is later glycosylated.

In an embodiment, the recombinant glycoprotein the glycosylation profile of which is modified by a method of any one of the previous embodiments is produced at large scale, meaning in a culture volume of at least 500 or 1,000 liters, preferably of at least 5,000 or 8,000 liters and most preferably of 10,000 or 20,000 liters.

In an embodiment, the recombinant glycoprotein the glycosylation profile of which is modified by a method of any one of the previous embodiments is produced at small scale or laboratory scale, meaning in a culture volume of 1, 5, 10 or 100 liters.

In an embodiment, the recombinant glycoprotein the glycosylation profile of which is modified by a method of any one of the previous embodiments is an immunoglobulin of the IgG type. In a preferred embodiment, the recombinant glycoprotein is an antibody. In a more preferred embodiment, the recombinant glycoprotein is a monoclonal antibody. In a most preferred embodiment, the recombinant glycoprotein is a therapeutic monoclonal antibody.

The cell culture of the method of any one of the previous embodiments, in which the recombinant glycoprotein is produced, can occur for 1 to 18 days, e.g. for 1, 2, 3, 4, 5, 6, 7, 8, 9, 10, 11, 12, 13, 14, 15, 16, 17, or 18 days. In an embodiment, the cell culture occurs for 4 to 18 days, e.g. for 4, 5, 6, 7, 8, 9, 10, 11, 12, 13, 14, 15, 16, 17, or 18 days. In a preferred embodiment, the cell culture occurs for 8 to 16 days, e.g. 8, 9, 10, 11, 12, 13, 14, 15, or 16 days. In a more preferred embodiment, the cell culture occurs for 10 to 14 days, e.g. 10, 11, 12, 13, or 14 days. In a most preferred embodiment, the cell culture of the method of any one of the previous embodiments occurs for 14 days.

Supplementation in the method of any one of the previous embodiments can occur from the beginning of the culture to the end of the culture either continuously or discontinuously. For example, one or more components of an additive or supplement can be added as a single bolus or two or more boli from a stock solution, while other components of the same additive or supplement can be added as part of a feed medium. In addition, any one or more components of an additive or supplement can be present in the basal medium from the beginning of the cell culture. Supplementation can thus occur at the beginning of a culture, and/or subsequent to the beginning of a culture, e.g. during the growth phase and/or the production phase.

In an embodiment, supplementation of the cell culture medium occurs from the start of the culture. In a preferred embodiment, the supplementation of the cell culture medium occurring from the start of the culture is with taurine. In a more preferred embodiment, the supplementation of the cell culture medium occurring from the start of the culture is with taurine at a final concentration of between 12.5 and 50 mM in the cell culture medium after supplementation. In a most preferred embodiment, the supplementation of the cell culture medium occurring from the start of the culture is with taurine at a final concentration of 25 mM in the cell culture medium after supplementation.

In an embodiment, supplementation of the culture medium occurs every 2nd day from a 3rd day of cultivation onwards, preferably as part of a feed. In a preferred embodiment, the supplementation of the culture medium occurring every 2nd day from a 3rd day of cultivation onwards is with fucose. In a more preferred embodiment, the supplementation of the culture medium occurring every 2nd day from a 3rd day of cultivation onwards is with fucose so that the concentration of fucose in the cell culture medium is raised by 0.4 to 1.6 mM. In a yet more preferred embodiment, the supplementation of the culture medium occurring every 2nd day from a 3rd day of cultivation onwards is with fucose so that the concentration of fucose in the cell culture medium is raised by 0.8 mM.

In a preferred embodiment, the supplementation of the culture medium occurs every 2nd day from a 3rd day of cultivation onwards until a 13th day of cultivation, preferably as part of a feed. In a more preferred embodiment, the supplementation of the culture medium occurring every 2nd day from a 3rd day of cultivation onwards until a 13th day of cultivation is with fucose. In a more preferred embodiment, the supplementation of the culture medium occurring every 2nd day from a 3rd day of cultivation onwards until a 13th day of cultivation is with fucose so that the concentration of fucose in the cell culture medium is raised by 0.4 to 1.6 mM. In a yet more preferred embodiment, the supplementation of the culture medium occurring every 2nd day from a 3rd day of cultivation onwards until a 13th day of cultivation is with fucose so that the concentration of fucose in the cell culture medium is raised by 0.8 mM.

In an embodiment, supplementation of the culture medium in the method of any one of the previous embodiments occurs every 2nd day from a 5th day of cultivation onwards, preferably as part of a feed. In a preferred embodiment, the supplementation of the culture medium occurring every 2nd day from a 5th day of cultivation onwards is with manganese. In a more preferred embodiment, the supplementation of the culture medium occurring every 2nd day from a 5th day of cultivation onwards is with manganese so that the concentration of manganese in the cell culture medium is raised by between 0.04 µM and 0.08 µM. In a yet more preferred embodiment, the supplementation of the culture medium occurring every 2nd day from a 5th day of cultivation onwards is with manganese so that the concentration of manganese in the cell culture medium is raised by 0.068 µM±0.01 µM.

In a preferred embodiment, supplementation of the culture medium occurs every 2nd day from a 5th day of cultivation onwards, until a 9th day of cultivation, preferably as part of a feed. In a more preferred embodiment, the supplementation of the culture medium occurring every 2nd day from a 5th day of cultivation onwards is with manganese. In a more preferred embodiment, the supplementation of the culture medium occurring every 2nd day from a 5th day of cultivation onwards is with manganese so that the concentration of manganese in the cell culture medium is raised by between 0.04 µM and 0.08 µM. In a yet more preferred embodiment, the supplementation of the culture medium occurring every 2nd day from a 5th day of cultivation onwards is with manganese so that the concentration of manganese in the cell culture medium is raised by 0.068 µM±0.01 µM.

In a preferred embodiment, supplementation of the culture medium with manganese in any one of the previous embodiments is supplementation with manganese as manganese chloride ($MnCl_2$). In a preferred embodiment, the supplementation with manganese as manganese chloride occurs every 2nd day from a 5th day of cultivation onwards, optionally until a $9^{th}$ day of cultivation, preferably as part of a feed. In a more preferred embodiment, the supplementation with manganese as manganese chloride occurs every 2nd day from a 5th day of cultivation onwards, optionally until a $9^{th}$ day of cultivation, so that the concentration of manganese in the cell culture medium is raised by between 0.04 µM and 0.08 µM. In a yet more preferred embodiment, the supplementation with manganese as manganese chloride occurs every 2nd day from a 5th day of cultivation onwards, optionally until a $9^{th}$ day of cultivation, so that the concentration of manganese in the cell culture medium is raised by 0.068 µM±0.01 µM.

In an embodiment, the supplementation of the culture medium in the method of any one of the previous embodiments occurs with taurine from the start of the culture, with fucose every second day from a $3^{rd}$ day of cultivation onwards, and with manganese, optionally as manganese chloride, every second day from a $5^{th}$ day of cultivation onwards. In a preferred embodiment, the supplementation of the culture medium occurs with taurine from the start of the culture, with fucose every second day from a $3^{rd}$ day of cultivation onwards until a $13^{th}$ day of cultivation, and with manganese, optionally as manganese chloride, every second day from a $5^{th}$ day of cultivation onwards until a $9^{th}$ day of cultivation, preferably each as part of a feed, respectively. In another preferred embodiment, the supplementation of the culture medium occurs with taurine from the start of the culture at a concentration in the cell culture medium after supplementation of 12.5 to 50 mM, with fucose every second day from a $3^{rd}$ day of cultivation onwards so that the concentration of fucose in the cell culture medium is raised by 0.4 to 1.6 mM, and with manganese, optionally as manganese chloride, every second day from a $5^{th}$ day of cultivation onwards so that the concentration of manganese in the cell culture medium is raised by between 0.04 µM and 0.08 µM. In a more preferred embodiment, the supplementation of the culture medium occurs with taurine from the start of the culture at a final concentration in the cell culture medium after supplementation of 12.5 to 50 mM, with fucose every second day from a $3^{rd}$ day of cultivation onwards until a $13^{th}$ day of cultivation so that the concentration of fucose in the cell culture medium is raised by 0.4 to 1.6 mM, and with manganese, optionally as manganese chloride, every second day from a $5^{th}$ day of cultivation onwards until a $9^{th}$ day of cultivation so that the concentration of manganese in the cell culture medium is raised by between 0.04 µM and 0.08 µM. In another preferred embodiment, the supplementation of the culture medium occurs with taurine from the start of the culture at a final concentration in the cell culture medium after supplementation of 25 mM, with fucose every second day from a $3^{rd}$ day of cultivation onwards so that the concentration of fucose in the cell culture medium is raised by 0.8 mM, and with manganese, optionally as manganese chloride, every second day from a $5^{th}$ day of cultivation onwards so that the concentration of manganese in the cell culture medium is raised by 0.068 µM±0.01 µM. In a most preferred embodiment, the supplementation of the culture medium occurs with taurine from the start of the culture at a final concentration in the cell culture medium after supplementation of 25 mM, with fucose every second day from a $3^{rd}$ day of cultivation onwards until a $13^{th}$ day of cultivation so that the concentration of fucose in the cell culture medium is raised by 0.8 mM, and with manganese, optionally as manganese chloride, every second day from a $5^{th}$ day of cultivation onwards until a $9^{th}$ day of cultivation so that the concentration of manganese in the cell culture medium is raised by 0.068 µM±0.01 µM.

In an embodiment, supplementation of the cell culture medium occurs during the production phase of the cell culture.

In an embodiment, the cell culture in the method of any one of the previous embodiments occurs between 35 to 40° C., e.g. at 35, 36, 37, 38, 39, or 40° C. or at any temperature there inbetween. In a preferred embodiment, the cell culture occurs between 36 and 38° C., e.g. 36, 37, or 38° C. or any temperature there inbetween. In a most preferred embodiment, the cell culture occurs at 37° C.

In an embodiment, the cell culture in the method of any one of the previous embodiments occurs at between pH 6 to 9, e.g. at pH 6, 7, 8, or 9. In a preferred embodiment, the cell culture occurs at pH 7.05±0.05.

In a particularly preferred embodiment, the cell culture of any one of the previous embodiments is a fed-batch culture.

In an embodiment, the glycoprotein in the method of any one of the previous embodiments is a VEGF antagonist, preferably an anti-VEGF antibody (see Examples 1-5). In a preferred embodiment, the fucosylation profile of the VEGF antagonist, preferably the anti-VEGF antibody is modified. In a more preferred embodiment, the modified fucosylation profile is at least 90%, preferably at least 95%, more preferably at least 96%, more preferably at least 98% of the fucosylation profile of the reference VEGF antagonist, preferably the anti-VEGF antibody. In another preferred embodiment, the galactosylation profile of the VEGF antagonist, preferably the anti-VEGF antibody is modified. In a more preferred embodiment, the modified galactosylation profile is at least 90%, preferably at least 95%, more preferably at least 96%, more preferably at least 98% of the galactosylation profile of the reference VEGF antagonist, preferably the anti-VEGF antibody. In another, yet more preferable embodiment, the fucosylation profile and the galactosylation profile of the VEGF antagonist, preferably the anti-VEGF antibody are modified. In a most preferred embodiment, the modified fucosylation profile is at least 90%, preferably at least 95%, more preferably at least 96%, more preferably at least 98% of the fucosylation profile of the reference VEGF antagonist, preferably the anti-VEGF antibody and the modified galactosylation profile is at least 90%, preferably at least 95%, more preferably at least 96%, more preferably at least 98% of the galactosylation profile of the reference VEGF antagonist, preferably the anti-VEGF antibody.

In an embodiment, the glycoprotein in the method of any one of the previous embodiments is an anti-CD20 antibody (see Example 6). In a preferred embodiment, the fucosylation profile of the anti-CD20 antibody is modified. In a more preferred embodiment, the modified fucosylation profile is at least 90%, preferably at least 95%, more preferably at least 96%, more preferably at least 98% of the fucosylation profile of the reference anti-CD20 antibody. In another preferred embodiment, the galactosylation profile of the anti-CD20 antibody is modified. In a more preferred embodiment, the modified galactosylation profile is at least 90%, preferably at least 95%, more preferably at least 96%, more preferably at least 98% of the galactosylation profile of the reference anti-CD20 antibody. In another, yet more preferable embodiment, the fucosylation profile and the galactosylation profile of the anti-CD20 antibody are modified. In a most preferred embodiment, the modified fucosylation profile is at least 90%, preferably at least 95%, more preferably at least 96%, more preferably at least 98% of the fucosylation profile of the reference anti-CD20 antibody and the modified galactosylation profile is at least 90%, preferably at least 95%, more preferably at least 96%, more preferably at least 98% of the galactosylation profile of the reference anti-CD20 antibody.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

The detailed description is merely exemplary in nature and is not intended to limit application and uses. The following examples further illustrate the present invention without, however, limiting the scope of the invention thereto. Various changes and modifications can be made by those skilled in the art on the basis of the description of the invention, and such changes and modifications are also included in the present invention.

Examples

1. Effect of Fucose Sources on Fucosylation Profile

To modulate the fucosylation profile of an anti-VEGF antibody to better resemble the fucosylation profile of a reference anti-VEGF antibody that has gained regulatory approval for therapeutic use in humans, in this case to be higher than when the anti-VEGF antibody is produced without culture medium supplementation, a series of fed-batch culture experiments were performed testing the impact of culture medium and feed supplementation with guanosine, fucose and mannose at different concentrations. Mannose and guanosine play critical roles in the de novo fucosylation pathway, mannose serving as substrate for the process and guanosine serving as a component of guanosine triphosphate, which is required for substrate activation in the enzymatic process, whereas fucose serves as a substrate for the so called salvage pathway of fucosylation (Gramer et al. Biotechnol Bioeng 108:1591-1602 (2011)).

Cell Culture

Cells

Chinese Hamster Ovary Cell line M (CHO-M), derived from common CHO K1 cells was purchased from Selexis (Selexis SA, Switzerland). The CHO-M cells were adapted to growth in serum-free, chemically-defined G11.2 basal medium (Irvine Scientific US). The CHO-M cell line was genetically engineered by transfection with recombinant DNA encoding for the anti-VEGF antibody to express the anti-VEGF antibody.

The experiments were performed at laboratory scale in AMBR small-scale shake flasks/laboratory bench top bioreactors (Sartorius Stedim Biotech GmbH, Goettingen, Germany) with 1-10 L working volume or in a 100 L process bioreactor. The production scale and maximum culture volume used in the examples was 5000 L.

Culturing Cells

The CHO-M cells were cultivated for 12 days under aerobic condition (dissolved oxygen (DO) level was set at 40% and controlled with an air and pure oxygen gas mixture). The level of $pCO_2$ was maintained under 60 mmHg by adjusting the aeration rate when necessary. Cells were cultivated at 37° C. During the whole cultivation period, the pH was maintained at 7.05±0.05 with 12.3% (w/w) $H_3PO_4$ solution or 0.5M $NaHCO_3$ base solution. To avoid glucose limitation and to keep the glucose level in the targeted 10-30 mM range, 35% (w/w) glucose solution was added to the culture, if necessary. Antifoam was used in case of foaming. The relevant metabolites were measured daily.

Fed-Batch Culture

Fed-batch cultures were performed by growing the cells initially in serum-free, chemically-defined basal medium G11.2 (Irvine Scientific US) for 12 days. Every second day from the 3rd day (post inoculation) of cultivation onward, concentrated feed solutions (Feed A and Feed B) were added to the culture medium in shot-wise mode.

Suppliers and Catalogue Numbers of media and additional supplements utilized in the examples are summarized below.

| | |
|---|---|
| G11.2 basal medium | Irvine Scientific, Cat No.: (customized) |
| HyClone ™ Cell Boost 7a feed supplement | GE Healthcare, Cat No.: SH31026 |
| HyClone ™ Cell Boost 7b feed supplement | GE Healthcare, Cat No.: SH31027 |
| NaHCO3 solution | Sigma-Aldrich, Cat No.: S8761 |
| L-glutamine (Gln; L-Gln) | Sigma-Aldrich, Cat No.: G5792 |
| Vitamin B12 | Sigma-Aldrich, Cat. No.: V6629 |
| NaOH solution | Sigma-Aldrich, Cat. No.: S72068 |
| Copper(II) sulfate pentahydrate ($CuSO_4 \cdot 5H_2O$) | Sigma-Aldrich, Cat. No.: C8027 |

The detailed composition of the basal medium and feeds can be found in Table 1.

TABLE 1

Compounds of basal medium, Feed A and Feed B (day 3, 5, 7, 9, 11, 13*).

| | Concentration |
|---|---|
| Basal Medium Compounds | |
| G11.2 basal medium powder | 19.98 [g/L] |
| NaHCO3 | 2.2 [g/L] |
| L-Glutamine | 1.17 [g/L] |

TABLE 1-continued

Compounds of basal medium, Feed A and Feed B
(day 3, 5, 7, 9, 11, 13*).

| | Concentration |
|---|---|
| Vitamine B12 | 7.8 [mg/L] |
| Pure Water | — |
| Feed A (day 3, 5, 7, 9, 11, 13*) | |
| Cell Boost 7a | 181.04 [g/L] |
| 5M NaOH | 18.6 [mL/L] |
| $CuSO_4*5H_2O$ | 0.5 [mg/L] |
| Pure Water | — |
| Feed B (day 3, 5, 7, 9, 11, 13*) | |
| Cell Boost 7 b | 96.4 [g/L] |
| 5M NaOH | 160.5 [mL/L] |
| Pure Water | |

*for 14 days of cultivation, see Example 4

On cultivation days 3, 5, 7, 9 and 11 the cell culture was fed with 4% of the total culture volume post-addition Feed A and 0.4% of the total culture volume post-addition Feed B, where Feed A was additionally supplemented with either guanosine (Sigma-Aldrich, Cat. No.: G6264), fucose (L-(−)-Fucose; Sigma-Aldrich, Cat. No.: F2252), or mannose (D-(+)-Mannose; Sigma-Aldrich, Cat. No.: M6020) at one of two different concentrations: guanosine at 20 or 60 mM, fucose at 10 or 20 mM, and mannose at 20 or 60 mM.

Purification

Protein a Chromatography

For quality analysis, the obtained antibody was affinity purified from the fermentation broth using Protein A chromatography. This capture offers an exceptional selectivity for Fc-bearing molecules, thereby removing more than 99.5% of contaminants in a single step.

Analytics

Viable Cell Density and Viability

Viable cell density and viability were determined by Countess™ Automated Cell Counter (Invitrogen Carlsbad, Calif., 2008) using Trypan blue staining method.

Glucose

Glucose concentration was measured by Cedex Bio HT Analyzer (Roche, Mannheim, Germany).

pCO2

Dissolved carbon-dioxide content (pCO2) was determined by ABL80 blood gas analyzer (Radiometer, Bronshoj, Denmark).

pH Measurement

At-line pH measurement for in situ pH meter re-calibration was performed with a S47 SevenMulti pH meter (Mettler Toledo, Zurich, Switzerland).

Osmolality

Osmolality was determined by Advanced Model 2020 multi-sample osmometer (Advanced Instruments, Norwood, Mass.).

Titer

Protein Titer was determined by Protein A affinity HPLC.

Glycosylation Profile

The N-glycan profile of the antibodies of the present invention was determined as follows: After denaturation and deglycosylation of the respective antibody samples via on-column digestion with PNGase F for 3 hours at 37° C., N-glycans were labeled with a fluorescent labeling reagent (2-AB). The excess dye was separated from the labeled N-glycans using cleanup cartridges (HILIC). The labeled, purified N-glycans were then separated using hydrophilic interaction liquid chromatography (HILIC-UHPLC) on amide stationary phase and the relative quantities of the labeled glycans were determined using fluorescence detection. Specifically, the antibodies (200 mg, 350 ml) were buffer exchanged with the aid of Nanosep® centrifugal devices (Pall, USA) to ammonium formate buffer (10 mM, pH 8.6). N-glycosidic-bound oligosaccharides were released by incubating 48-ml samples with 2 ml PNGase F (500,000 U/ml, New England Biolabs) at 45° C. for 1 h. Released glycans were labeled with 2-AB at 65° C. for 2 h (Glyko® Signal 2-AB Labeling Kit, ProZyme). Excess 2-AB was removed using HyperSep-96 Diol cartridges (Thermo) with a vacuum station. Labeled glycans were washed with 96% acetonitrile, eluted from the cartridges and analyzed by HILIC-UHPLC using a Waters BEH Glycan Separation Technology column (2.1×150 mm, 1.7 mm) on a Dionex RSLC Ultimate 300016 or a Waters ACQUITY UPLC® system. A 45-min acetonitrile gradient was applied and fluorescence signals were detected at 420 nm (excitation at 330 nm). Peaks were integrated automatically according to pre-defined parameters with the software Chromeleon© and relative glycan compositions were calculated. HILIC and HILIC-UHPLC are described in greater detail in Reusch et al., mAbs, 7(1), 2015, 167-179.

The amount of the released glycans was calculated using Area % values of the corresponding peaks. The four main glycans of the antibodies of the present invention (G0F, G1F, G1'F, G2F) were evaluated in comparison to the respective reference antibodies. Acceptance criteria for the anti-VEGF antibody were: G0F: ≥73.4 area %, G1F: 4-12.9 area %, G1'F: 2.3-5.6 area %, G2F: 0.5-1.7 area %, Total Main Afucosylated (MAF): 1.9-3.7 area %. Acceptance criteria for the anti-CD20 antibody were: G0F: 40-56 area %; G1F: 28-38 area %; G1'F: 9-13 area % and G2F: 5-12 area %.

Results

The impact of the different supplements on total main afucosylated forms of the anti-VEGF antibody after 12 days of cultivation is shown in FIG. 1.

The fed-batch culture experiments showed that the fucose supplemented feed led to the most prominent reduction of total main afucosylated forms (MAF) of the anti-VEGF antibody as compared to the tested fucose alternatives guanosine and mannose. The guanosine supplemented feed appeared to be second best in reducing the total MAF at the higher tested concentration of 60 mM. This was in contrast to the measured result after the fucose supplemented feed, where the reduction in total MAF was most effective at the lower tested fucose concentration at 10 mM. The same was true in the case of mannose, where the lower concentration of 20 mM was more efficient in reducing the total main afucosylated forms compared to the 60 mM mannose supplemented feed. Accordingly, fucose was selected for further experimentation.

2. Concentration-Dependent Effect of Fucose on Fucosylation Profile

To further analyse the effect of fucose on fucosylation profile of the anti-VEGF antibody, a series of fed-batch culture experiments were performed testing the impact of feed medium supplementation with varying concentrations of fucose.

Unless otherwise indicated, cell culture, isolation and analytics were performed as in the above example.

Fed-batch cultures were performed for 12 days. On cultivation days 3, 5, 7, 9 and 11 the cell culture was fed with 4% of the total culture volume post-addition Feed A and 0.4% of the total culture volume post-addition Feed B, where Feed A was additionally supplemented with fucose (L-(−)-Fucose; Sigma-Aldrich, Cat. No.: F2252) at a concentration of either 10 mM, 20 mM or 40 mM.

Results

Figure 2:
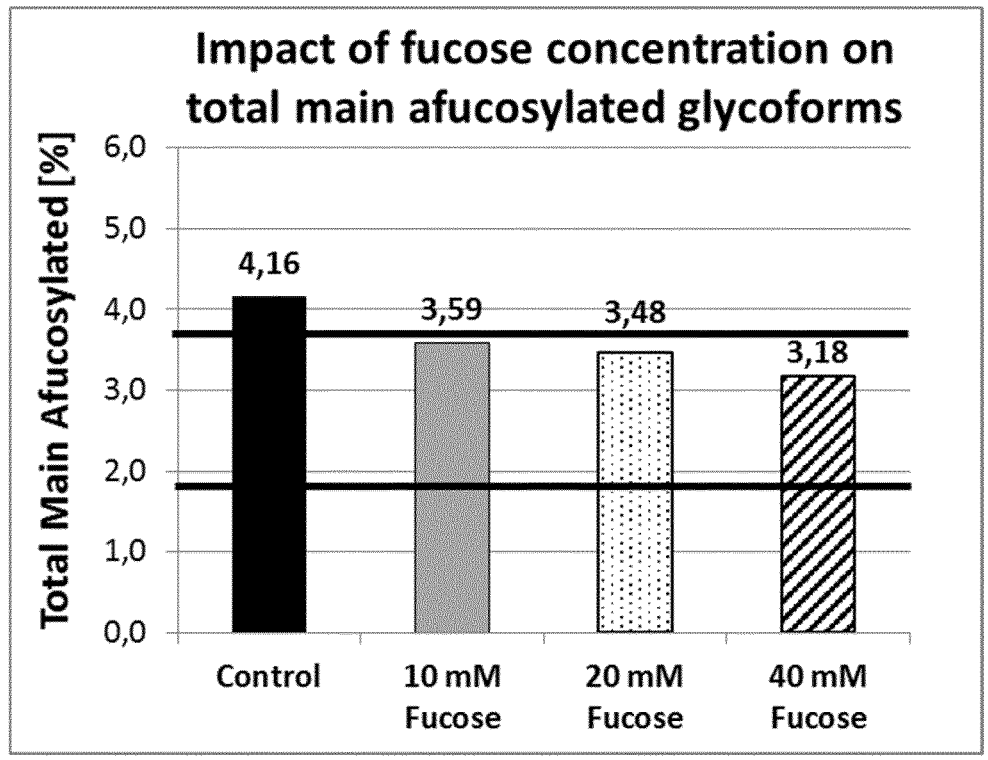
FIG. 2: Impact of different fucose concentrations on total main afucosylated (MAF) glycoforms of the anti-VEGF antibody of the present invention. Results are derived from day 12 of cultivation. Black bar: Control batches without fucose supplementation of the feed medium; Grey bar: Batches fed with 10 mM fucose supplemented feed medium; Dotted bar: Batches fed with 20 mM fucose supplemented feed medium; Diagonally striped bar: Batches fed with 40 mM fucose supplemented feed medium. Black lines: Ranges of total main afucosylated (MAF) glycoforms of the reference anti-VEGF antibody of the present invention.

The concentration-dependent decrease in total main afucosylated forms of the anti-VEGF antibody upon the addition of the respective fucose containing feeds is shown in FIG. 2.

The biosimilarity of the anti-VEGF antibody compared to the aforementioned reference anti-VEGF antibody was improved in terms of total main afucosylated forms (MAF), i.e. fucosylation profile. The fed-batch culture experiments showed that, compared to the control experiment where the culture medium lacks fucose, the total main afucosylated forms of the anti-VEGF antibody as measured on day 12 of cultivation were decreased by the feed of fucose at all tested concentrations, which led to a better resemblance to the amount of total MAF of the reference anti-VEGF antibody. This decrease of total MAF was concentration-dependent, as the most prominent reduction was achieved when feeding fucose at a concentration of 40 mM. However, to avoid an increase in cell culture osmolality and the undesired side effects that come with it, a feed supplemented with fucose at a concentration of 20 mM was chosen for further experiments. Although feed supplementation with 20 mM fucose led to a fucosylation profile of the anti VEGF antibody, which better resembled the fucosylation profile of the reference anti-VEGF antibody, the degree of galactosylation of the anti-VEGF antibody was below acceptable compared to the reference anti-VEGF antibody.

3. Concentration-Dependent Effect of Manganese on Glycosylation Profile

To modify the galactosylation profile of the anti-VEGF antibody to better resemble the galactosylation profile of the reference anti-VEGF antibody, a series of fed-batch culture experiments were performed testing the impact of feed supplementation with varying concentrations of manganese, a cofactor for beta-1,4-galactosyltransferase, at varying times.

Unless otherwise indicated, cell culture, isolation and analytics were performed as in Example 1.

Fed-batch cultures were performed for 11 days. Manganese was supplemented to Feed A in the form of manganese (II) chloride tetrahydrate (MnCl$_2$*4H$_2$O; Sigma-Aldrich, Cat. No.: M5005) on cultivation days 3, 5, 7, and 9; 5, 7, and 9; 7 and 9; or 9 at the concentration indicated in Table 2.

Results

The results of the glycosylation profile analysis upon feed supplementation with manganese are shown in Table 2. The most favorable effect of manganese addition on galactosylation can be observed between the 5th and 9th day of cultivation, in the period where cells can be characterized with the highest specific productivity. As a consequence, Feed A was supplemented in the subsequent fed-batch experiments with 1.7 µM manganese chloride on cultivation days 5, 7 and 9. Although the galactosylation profile of the anti-VEGF antibody could be improved through feed supplementation with manganese, it can also be seen that manganese addition causes a considerable increase in the level of afucosylated glycoforms (e.g. G0 increases with manganese, G0F decreases with manganese). Further culture media supplementation had to be considered to modify the fucosylation profile of the anti-VEGF antibody to better resemble the fucosylation profile of the reference anti-VEGF antibody.

TABLE 2

Effect of different MnCl$_2$*4H$_2$O supplementation strategies on the glycosylation profile of the anti-VEGF antibody. The indicated concentration values refer to the MnCl$_2$*4H$_2$O content of Feed A solution.

| Mn2+ feed supplementation [day] | Mn2+ [µM/feed] | G0 [%] | G0F [%] | G1F [%] | G1'F [%] | G2F [%] | ΣAF [%] |
|---|---|---|---|---|---|---|---|
| 3-5-7-9 | 0 | 3.32 | 79.84 | 4.47 | 2.41 | 0.37 | 3.85 |
| 3-5-7-9 | 0.625 | 4.53 | 78.15 | 6.28 | 3.12 | 0.59 | 5.19 |
| 3-5-7-9 | 1.25 | 4.79 | 73.57 | 9.70 | 4.31 | 1.16 | 5.69 |
| 3-5-7-9 | 2.5 | 4.72 | 69.05 | 12.64 | 5.27 | 1.89 | 5.91 |
| 5-7-9 | 0 | 3.56 | 79.98 | 4.78 | 2.52 | 0.40 | 4.12 |
| 5-7-9 | 0.83 | 4.61 | 77.19 | 7.17 | 3.42 | 0.69 | 5.34 |
| 5-7-9 | 1.67 | 4.78 | 74.37 | 9.16 | 4.12 | 1.02 | 5.66 |
| 5-7-9 | 3.3 | 4.82 | 71.61 | 10.99 | 4.73 | 1.49 | 5.82 |
| 7-9 | 0 | 3.50 | 79.75 | 4.82 | 2.54 | 0.40 | 4.10 |
| 7-9 | 1.25 | 4.29 | 79.50 | 5.75 | 2.93 | 0.47 | 4.94 |
| 7-9 | 2.5 | 4.42 | 77.18 | 7.65 | 3.60 | 0.73 | 5.20 |
| 7-9 | 5 | 4.61 | 74.79 | 9.01 | 4.04 | 1.07 | 5.51 |
| 9 | 0 | 3.36 | 79.30 | 4.86 | 2.53 | 0.39 | 3.95 |
| 9 | 2.5 | 4.10 | 80.27 | 5.02 | 2.64 | 0.42 | 4.70 |
| 9 | 5 | 4.29 | 79.94 | 5.51 | 2.81 | 0.47 | 4.92 |
| 9 | 10 | 4.62 | 79.24 | 5.41 | 2.74 | 0.55 | 5.27 |
| Reference* | min. | 1.6 | 73.4 | 4.0 | 2.3 | 0.5 | 1.9 |
|  | max. | 2.9 |  | 12.9 | 5.6 | 1.7 | 3.7 |

*calculated from the mean and standard deviation of the glycosylation profiles of 9 commercially available anti-VEGF antibody batches.

4. Effect of Taurine Supplementation on Fucosylation Profile

To cope with undesired increases in osmolality and further suppression of fucosylation upon the prolongation of the cell cultivation time towards 14 days as planned for the subsequent experiments, a series of fed-batch culture experiments was conducted where the cell culture medium was supplemented with an osmoprotectant. Taurine was selected as a possible osmoprotectant because it was known from the art that taurine supplementation can also increase the titer of glycoproteins produced in cell culture.

Unless otherwise indicated, cell culture, isolation and analytics were performed as in Example 1.

Fed-Batch cultures were performed for 14 days. Taurine (Sigma-Aldrich, Cat. No.: T4571) was supplemented to the culture medium at the start of the culture (day 0 post inoculum) at a concentration of 12.5 mM, 25 mM or 50 mM. In addition, manganese was supplemented to Feed A in the form of manganese (II) chloride tetrahydrate (MnCl$_2$*4H$_2$O; Sigma-Aldrich, Cat. No.: M5005) on cultivation days 5, 7, and 9 at a concentration of 1.7 µM.

Results

Figure 3:
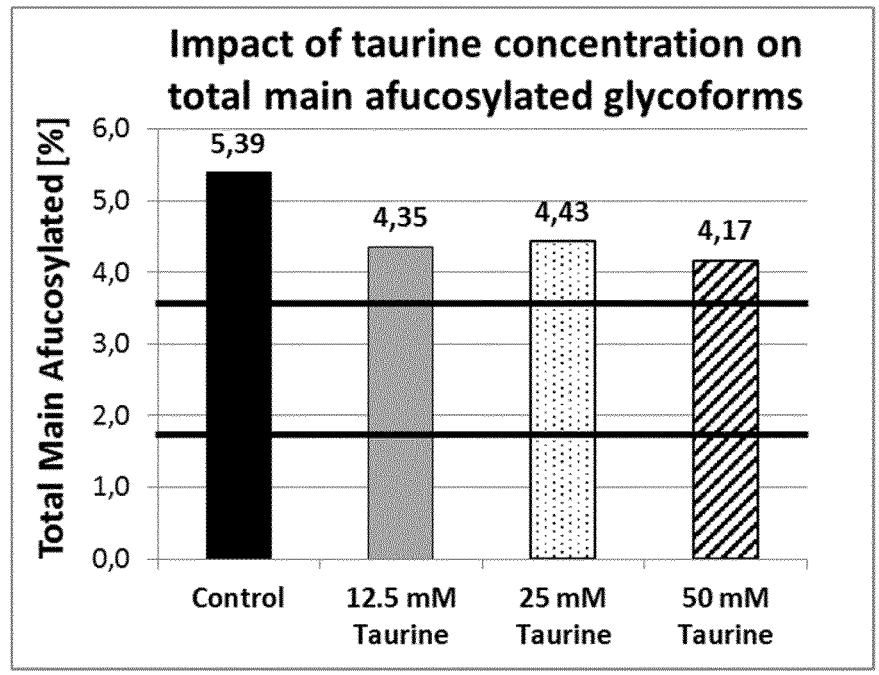
FIG. 3: Impact of different taurine concentrations on total main afucosylated (MAF) glycoforms of the anti-VEGF antibody of the present invention. Results are derived from day 14 of cultivation. Black bar: Control batches without taurine supplemented culture medium; Grey bar: Batches cultured with 12.5 mM taurine supplemented culture medium; Dotted bar: Batches cultured with 25 mM taurine supplemented culture medium; Diagonally striped bar: Batches cultured with 50 mM taurine supplemented culture medium. Black lines: Ranges of total main afucosylated (MAF) glycoforms of the reference anti-VEGF antibody of the present invention.

The concentration-dependent impact on total main afucosylated forms of the anti-VEGF antibody upon taurine supplementation of the basal medium is shown in FIG. 3.

Surprisingly, a concentration-dependent decrease in total main afucosylated forms of the anti-VEGF antibody upon taurine supplementation of the basal medium was observed. The fed-batch culture experiments showed that compared to cultivation in basal medium lacking taurine, the amount of total main afucosylated forms (MAF) of the anti-VEGF antibody after 14 days of cultivation was decreased in all taurine supplemented cultures. The high concentration taurine supplementation (50 mM) showed a fucosylation profile, which was closest to the respective range of the fucosylation profile of the reference anti-VEGF antibody. Nevertheless, for the next experiments a concentration of 25 mM taurine was chosen for culture medium supplementation to avoid further increases in cell culture osmolality and preserve the action of taurine as an osmoprotectant.

5. Effect of Fucose, Manganese, and Taurine Supplementation on Glycosylation Profile Next, the modifiability of the glycosylation profile of the anti-VEGF antibody through taurine supplementation of the basal medium in addition to the feed supplementation with fucose and manganese was investigated.

Unless otherwise indicated, cell culture, isolation and analytics were performed as in Example 1.

Cell Culture

Cells

Chinese Hamster Ovary Cell line M (CHO-M), derived from common CHO K1 cells was purchased from Selexis (Selexis SA, Switzerland). The CHO-M cells were adapted to growth in serum-free, chemically-defined G11.2 basal medium (Irvine Scientific US). The CHO-M cell line was genetically engineered by transfection with recombinant DNA encoding for the anti-VEGF antibody to express the anti-VEGF antibody.

Fed-Batch Culture

Fed-batch cultures were performed for 14 days by growing the cells in serum-free, chemically-defined basal medium G11.2 (Irvine Scientific US) supplemented with 25 mM taurine (Sigma-Aldrich, Cat. No.: T4571) at the start of the culture (day 0 post inoculum).

Every second day from the 3rd day (post inoculation) of cultivation onward, 4% of the total culture volume post-addition Feed A supplemented with 20 mM fucose and 0.4% of the total culture volume post-addition Feed B were added separately to the culture medium in shot-wise mode. In addition, manganese was supplemented to Feed A in the form of manganese (II) chloride tetrahydrate ($MnCl_2*4H_2O$; Sigma-Aldrich, Cat. No.: M5005) on days 5, 7 and 9 (post inoculation) of cultivation at a concentration of 1.7 µM in Feed A.

Suppliers and Catalogue Numbers of media and additional supplements utilized in Example 5 are summarized below.

| | |
|---|---|
| G11.2 basal medium | Irvine Scientific, Cat No.: (customized) |
| HyClone ™ Cell Boost 7a feed supplement | GE Healthcare, Cat No.: SH31026 |
| HyClone ™ Cell Boost 7b feed supplement | GE Healthcare, Cat No.: SH31027 |
| NaHCO3 solution | Sigma-Aldrich, Cat No.: S8761 |
| L-glutamine (Gln; L-Gln) | Sigma-Aldrich, Cat No.: G5792 |
| Vitamin B12 | Sigma-Aldrich, Cat. No.: V6629 |
| NaOH solution | Sigma-Aldrich, Cat. No.: S72068 |
| Copper(II) sulfate pentahydrate | Sigma-Aldrich, Cat. No.: C8027 ($CUSO_4*5H_2O$) |
| Taurine | Sigma-Aldrich, Cat. No.: T4571 |
| L-Fucose | Sigma-Aldrich, Cat. No.: F2252 |
| Manganese (II) chloride tetrahydrate ($MnCl_2*4H_2O$) | Sigma-Aldrich, Cat. No.: M5005 |

The detailed composition of the basal medium and feeds used in Example 5 can be found in Table 3.

TABLE 3

Compounds of basal medium, Feed A (day 3, 11, 13), Feed A (day 5, 7, 9) and Feed B (day 3, 5, 7, 9, 11, 13) solutions

| | Concentration |
|---|---|
| Basal medium compounds | |
| G11.2 basal medium powder | 19.98 [g/L] |
| NaHCO3 | 2.2 [g/L] |
| L-Glutamine | 1.17 [g/L] |
| Vitamine B12 | 7.8 [mg/L] |
| Taurine | 3.14 [g/L] |
| Pure Water | — |
| Feed A (day 3, 11, 13) | |
| Cell Boost 7a | 181.04 [g/L] |
| 5M NaOH | 18.6 [mL/L] |
| L-Fucose | 3.28 [g/L] |
| $CuSO_4*5H_2O$ | 0.5 [mg/L] |
| Pure Water | — |
| Feed A (day 5, 7, 9) | |
| Cell Boost 7a | 181.04 [g/L] |
| 5M NaOH | 18.6 [mL/L] |
| L-Fucose | 3.28 [g/L] |
| $CuSO_4*5H_2O$ | 0.5 [mg/L] |
| $MnCl_2*4H_2O$ | 333 [µg/L] |
| Pure Water | — |
| Feed B (day 3, 5, 7, 9, 11, 13) | |
| Cell Boost 7b | 94.6 [g/L] |
| 5M NaOH | 160.5 [mL/L] |
| Pure Water | — |

Results

Figure 4:
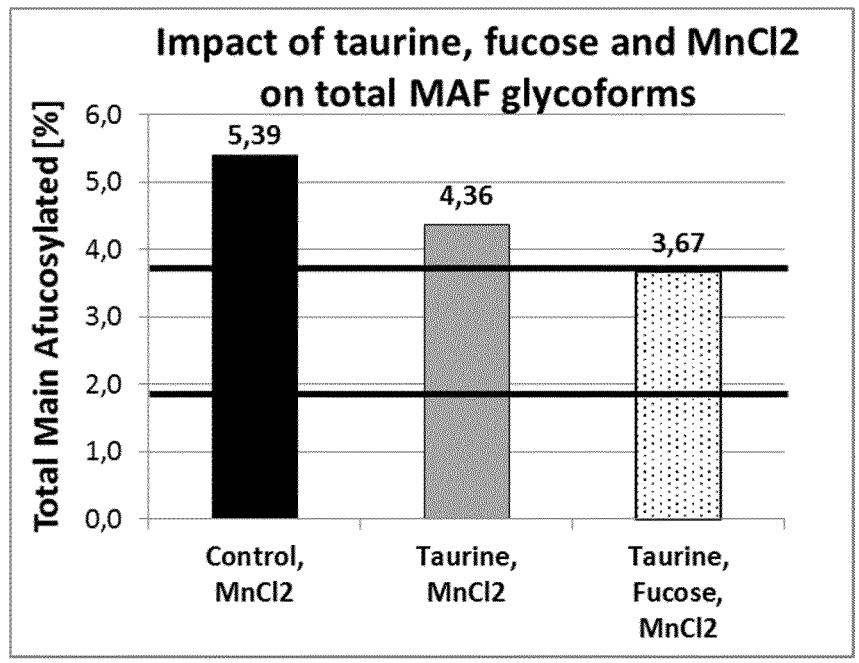
FIG. 4: Impact of taurine, fucose and manganese on total main afucosylated (MAF) glycoforms of the anti-VEGF antibody of the present invention. Results are derived from day 14 of cultivation. Black bar: Control batches fed with 1.7 µM manganese chloride supplemented feed medium but without fucose and taurine; Grey bar: Batches cultured with 25 mM taurine supplemented culture medium, and fed with 1.7 µM manganese chloride supplemented feed medium but without fucose supplemented feed medium; Dotted bar: Batches cultured with 25 mM taurine supplemented culture medium and fed with 20 mM fucose and 1.7 µM manganese chloride supplemented feed medium. Black lines: Ranges of total main afucosylated (MAF) glycoforms of the reference anti-VEGF antibody of the present invention.

The effect of taurine, fucose and manganese on total main afucosylated forms of the anti-VEGF antibody is shown in FIG. 4.

The fed-batch culture experiments showed that, compared to cultivation in basal medium lacking taurine and fucose, the amount of total main afucosylated forms (MAF) of the anti-VEGF antibody after 14 days of cultivation could be decreased through addition of 25 mM taurine to the basal medium. In addition, the amount of total MAF of the anti-VEGF antibody could be reduced further through the implementation of 20 mM fucose feeds to the taurine containing cell culture. The synergistic effect of the addition of taurine and fucose to the cell culture led to a fucosylation profile that fits well within the respective range of the fucosylation profile of the reference anti-VEGF antibody.

Figure 5:
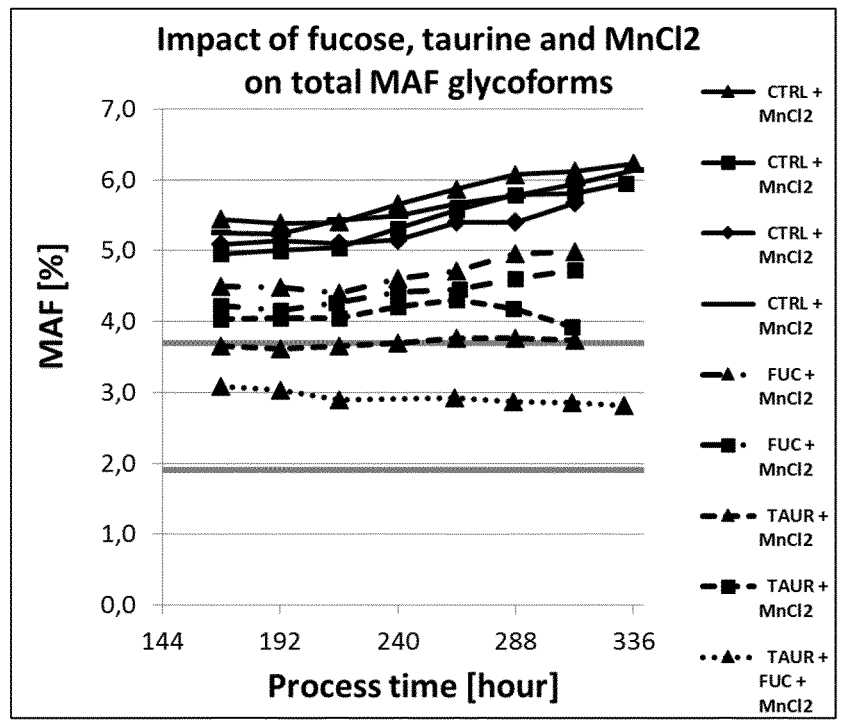
FIG. 5: Total main afucosylated profiles (MAF) of the produced anti-VEGF antibody of the present invention. Results are derived from daily sample analysis from day 7 to day 13 of cultivation, or from day 7 to day 14 of cultivation, respectively. Black lines: control batches without taurine and fucose but fed with manganese supplemented feed medium; Dotted and striped lines: batches fed with fucose and manganese supplemented feed medium; Striped lines: batches cultured with taurine supplemented culture medium and fed with manganese supplemented feed medium; Dotted line: batches cultured with taurine supplemented culture medium and fed with manganese and fucose supplemented feed medium. Grey lines: Ranges of total main afucosylated glycoforms of the reference anti-VEGF antibody of the present invention.

FIG. 5 illustrates the fucosylation profile according to a daily analysis of samples of the fermentation broth from the 3rd day (post inoculum) of cultivation onwards.

The analysis shows that feed supplementation with fucose at 20 mM, in combination with feed supplementation of manganese at 1.7 µM and culture medium supplementation with taurine at 25 mM in combination with feed supplementation of manganese at 1.7 µM could reduce total main afucosylated glycoforms (MAF) alone (dotted and striped lines as well as striped lines in FIG. 5). However, the lowest MAF profile was observed only when all three components were supplemented together (dotted line in FIG. 5). This MAF profile was well within the range of the total MAF profile, i.e. at least 90%, preferably at least 95%, more preferably at least 96%, more preferably at least 98% of the fucosylation profile of the reference anti-VEGF antibody.

Figure 6:
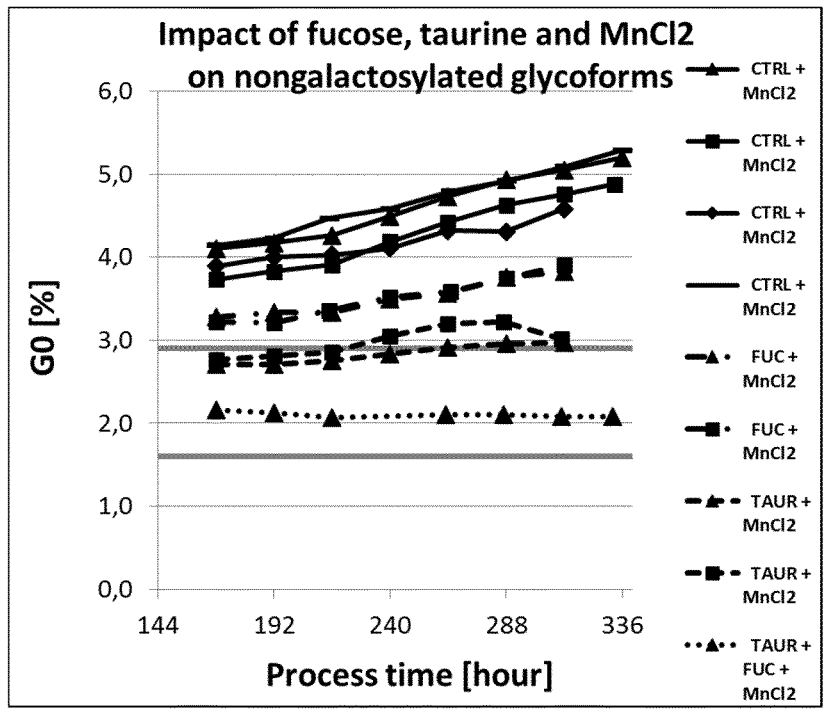
FIG. 6: Nongalactosylated glycoform (G0) profiles of the produced anti-VEGF antibody of the present invention. Results are derived from daily sample analysis from day 7 to day 13 of cultivation, or from day 7 to day 14 of cultivation, respectively. Black lines: control batches without taurine and fucose but fed with manganese supplemented feed medium; Dotted and striped lines: batches fed with fucose and manganese supplemented feed medium; Striped lines: batches cultured with taurine supplemented culture medium and fed with manganese supplemented feed medium; Dotted line: batches cultured with taurine supplemented culture medium and fed with manganese and fucose supplemented feed medium. Grey lines: Ranges of nongalactosylated (G0) glycoforms of the reference anti-VEGF antibody of the present invention.

Similarly, the profile of non-galactosylated glycoforms (G0) of the respective samples according daily analysis are shown in FIG. 6.

The experiments show that feed supplementation with fucose at 20 mM, in combination with feed supplementation of manganese at 1.7 µM and culture medium supplementation with taurine at 25 mM in combination with feed supplementation of manganese at 1.7 µM could reduce the amount of non-galactosylated glycoforms (G0) alone (dotted and striped lines as well as striped lines in FIG. 6). Nevertheless, the lowest G0 profile, which is within the range of the galactosylation profile, i.e. at least 90%, preferably at least 95%, more preferably at least 96%, more preferably at least 98% of the galactosylation profile of the reference anti-VEGF antibody, was observed only when all three components had been supplemented in the culture medium and the feed, respectively (dotted line in FIG. 6). Altogether, through combined supplementation of the culture with taurine, manganese and fucose, similarity of the anti-VEGF antibody to the reference anti-VEGF antibody could be improved in view of the profile of non-galactosylated glycoforms (G0), i.e. galactosylation profile.

6. Effect of Fucose, Manganese, and Taurine Supplementation on Glycosylation Profile In analogous fed-batch experiments with an anti-CD20 antibody, the same effect regarding the modification of the glycosylation profile upon supplementation of the culture medium with fucose, manganese and taurine could be achieved.

Unless otherwise indicated, cell culture, feeding schemes, isolation and analytics were performed as described in Example 5.

Fed-batch cultures were performed for 12 days by growing the cells in serum-free, chemically-defined basal medium G11.2 (Irvine Scientific US) supplemented with 25 mM taurine (Sigma-Aldrich, Cat. No.: T4571) at the start of the culture (day 0 post inoculum).

Every second day from the 3rd day (post inoculation) of cultivation onward, 4% of the total culture volume post-addition Feed A supplemented with 20 mM fucose and 0.4% of the total culture volume post-addition Feed B were added separately to the culture medium in shot-wise mode. In addition, manganese was supplemented to Feed A in the form of manganese (II) chloride tetrahydrate ($MnCl_2 \cdot 4H_2O$; Sigma-Aldrich, Cat. No.: M5005) on days 5, 7 and 9 (post inoculation) of cultivation at a concentration of 1.7 µM in Feed A.

Results

Table 4 shows the effect of different feed supplementation strategies on the glycosylation profile of the anti-CD20 antibody based on the daily analysis of samples of the fermentation broth from the $3^{rd}$ day (post inoculum) of cultivation onwards.

The glycoanalysis reveals that 3 or 4 days of cultivation in taurine supplemented culture medium fed with a fucose supplemented feed had no effect on the fucosylation profile and the galactosylation profile of the anti-CD20 antibody. Only from day 5 of cultivation onwards, when a fucose and manganese supplemented feed was added to the cell culture, in other words, when all three components fucose, manganese and taurine were present in the cell culture the fucosylation profile and the galactosylation profile of the anti-CD20 antibody could be modified to better resemble the respective fucosylation profile and galactosylation profile of a reference anti-CD20 antibody.

TABLE 4

Effect of fucose, manganese and taurine supplementation on glycosylation profile of the anti-CD20 antibody

| Basal Medium Supplementation | Feed A Supplementation | Feeding Time [day] | Process time [day] | G0F [%] | G1F [%] | G1'F [%] | G2F [%] |
|---|---|---|---|---|---|---|---|
| Taurine | Fucose | 3 | 3 | 63.94 | 24.17 | 8.62 | 3.27 |
| | | 3 | 4 | 63.20 | 24.66 | 8.80 | 3.34 |
| | Fucose + $MnCl_2$ | 5, 7, 9 | 5 | 57.80 | 27.72 | 9.66 | 4.50 |
| | | 5, 7, 9 | 6 | 54.99 | 29.86 | 10.17 | 4.98 |
| | | 5, 7, 9 | 7 | 51.71 | 31.74 | 10.66 | 5.89 |
| | | 5, 7, 9 | 8 | 53.09 | 30.84 | 10.43 | 5.64 |
| | | 5, 7, 9 | 9 | 53.32 | 30.71 | 10.40 | 5.57 |
| | | 5, 7, 9 | 10 | 54.28 | 29.95 | 10.23 | 5.54 |
| Reference* | | min. | | 40 | 28 | 9 | 5 |
| | | max. | | 56 | 38 | 13 | 12 |

*calculated from the mean and standard deviation of the glycosylation profiles of 13 commercially available anti-CD20 antibody batches

The invention claimed is:

1. A method for modifying the glycosylation profile of a recombinant glycoprotein produced in cell culture comprising:
   culturing eukaryotic cells expressing the recombinant glycoprotein in a cell culture medium, wherein the cell culture medium is supplemented with fucose, manganese, and taurine,
   wherein the glycosylation profile comprises a fucosylation profile and/or galactosylation profile, and
   wherein the fucosylation profile and/or galactosylation profile of the produced recombinant glycoprotein is modified to better resemble the fucosylation profile and/or galactosylation profile of a reference glycoprotein than when the eukaryotic cells expressing the recombinant glycoprotein are cultured without fucose, manganese, and taurine supplementation.

2. The method of claim 1, wherein the modified fucosylation profile is at least 90% of the fucosylation profile of the reference glycoprotein and/or the modified galactosylation profile is at least 90% of the galactosylation profile of the reference glycoprotein.

3. The method of claim 1, wherein the concentration of fucose in the culture medium is raised by between 0.4 mM and 1.6 mM through supplementation.

4. The method of claim 1, wherein the concentration of manganese in the culture medium is raised by between 0.02 µM and 0.1 µM through supplementation.

5. The method of claim 1, wherein the final concentration of taurine in the culture medium after supplementation is between 12.5 mM and 50 mM.

6. The method of claim 1, wherein the method further comprises a step of isolating the produced recombinant glycoprotein from the cell culture.

7. The method of claim 1, wherein the eukaryotic cells are Chinese hamster ovary (CHO) cells.

8. The method of claim 1, wherein the recombinant glycoprotein is produced at a large scale.

9. The method of claim 1, wherein the recombinant glycoprotein is an immunoglobulin of the IgG type.

10. The method of claim 1, wherein the recombinant glycoprotein is a monoclonal antibody, optionally a therapeutic monoclonal antibody.

11. The method of claim 1, wherein the cell culture occurs for 14 days.

12. The method of claim 1, wherein the supplementation of the culture medium occurs every 2nd day from a 3rd day of cultivation onwards, optionally until a 13th day of cultivation.

13. The method of claim 1, wherein the manganese is supplemented as manganese chloride ($MnCl_2$) and wherein the supplementation of the culture medium with $MnCl_2$ occurs every 2nd day from a 5th day of cultivation onwards, optionally until a 9th day of cultivation.

14. The method of claim 1, wherein the supplementation of the culture medium occurs during the production phase of the cell culture.

15. The method of claim 1, wherein the cell culture occurs at 37° C.

16. The method of claim 1, wherein the cell culture medium has a pH of 7.05±0.05.

17. The method of claim 1, wherein the cell culture is a fed-batch culture.

18. The method of claim 1, wherein the glycoprotein is a VEGF antagonist.

19. The method of claim 18, wherein the modified fucosylation profile is at least 90% of the fucosylation profile of the reference VEGF antagonist and/or the modified galactosylation profile is at least 90% of the galactosylation profile of the reference VEGF antagonist.

20. The method of claim 1, wherein the glycoprotein is an anti-CD20 antibody.

21. The method of claim 20, wherein the modified fucosylation profile is at least 90% of the fucosylation profile of the reference anti-CD20 antibody and/or the modified galactosylation profile is at least 90% of the galactosylation profile of the reference anti- CD20 antibody.

* * * * *

UNITED STATES PATENT AND TRADEMARK OFFICE
CERTIFICATE OF CORRECTION

PATENT NO. : 12,168,791 B2  
APPLICATION NO. : 17/292302  
DATED : December 17, 2024  
INVENTOR(S) : László Párta et al.

Page 1 of 1

It is certified that error appears in the above-identified patent and that said Letters Patent is hereby corrected as shown below:

On the Title Page

Item (72), delete "Gyömr (HU)" and insert -- Gyömrö (HU) --, therefor.

Signed and Sealed this  
Eleventh Day of March, 2025

Coke Morgan Stewart  
*Acting Director of the United States Patent and Trademark Office*